US010182571B2

(12) United States Patent
Grossi de Sá et al.

(10) Patent No.: US 10,182,571 B2
(45) Date of Patent: Jan. 22, 2019

(54) METHOD AND COMPOSITIONS FOR THE GENETIC CONTROL OF INSECT PESTS IN COTTON PLANTS BY CHITIN SYNTHASE GENE SILENCING

(71) Applicant: EMPRESA BRASILEIRA DE PESQUISA AGROPECUÁRIA—EMBRAPA, Brasilia-DF (BR)

(72) Inventors: Maria Fátima Grossi de Sá, Brasilia-DF (BR); Maria Cristina Mattar Da Silva, Brasilia-DF (BR); Leonardo Lima Pepino de Macedo, Brasilia-DF (BR); Alexandre Augusto Pereira Firmino, Brasilia-DF (BR); Roberta Ramos Coelho, Brasilia-DF (BR); Isabela Tristan Lourenço, Brasilia-DF (BR)

(73) Assignee: EMPRESA BRASILEIRA DE PESQUISA AGROPECUÁRIA—EMBRAPA, Brasília-DF (BR)

( * ) Notice: Subject to any disclaimer, the term of this patent is extended or adjusted under 35 U.S.C. 154(b) by 170 days.

(21) Appl. No.: 14/653,699

(22) PCT Filed: Dec. 27, 2013

(86) PCT No.: PCT/BR2013/000608

§ 371 (c)(1),
(2) Date: Jun. 18, 2015

(87) PCT Pub. No.: WO2014/100879

PCT Pub. Date: Jul. 3, 2014

(65) Prior Publication Data

US 2016/0000086 A1 Jan. 7, 2016

(30) Foreign Application Priority Data

Dec. 28, 2012 (BR) ...................... 10 2012 033539 5

(51) Int. Cl.

| | |
|---|---|
| ***C12N 15/82*** | (2006.01) |
| ***A01N 57/16*** | (2006.01) |
| ***C12N 15/113*** | (2010.01) |
| ***C07K 14/435*** | (2006.01) |
| ***A23K 10/30*** | (2016.01) |
| ***A23L 19/00*** | (2016.01) |

(52) U.S. Cl.
CPC .............. *A01N 57/16* (2013.01); *A23K 10/30* (2016.05); *A23L 19/00* (2016.08); *C07K 14/43563* (2013.01); *C12N 15/113* (2013.01); *C12N 15/1137* (2013.01); *C12N 15/8286* (2013.01); *A23V 2002/00* (2013.01); *C12N 2310/14* (2013.01); *C12N 2330/51* (2013.01); *Y02A 40/162* (2018.01)

(58) Field of Classification Search
CPC ...................................................... A01N 57/16
USPC ......................................................... 800/279
See application file for complete search history.

(56) References Cited

U.S. PATENT DOCUMENTS

2008/0168583 A1* 7/2008 Fincher ................ C07K 14/415
800/278

OTHER PUBLICATIONS

GenBank Accession No. DQ062153.1 2005.*
Colliver et al. Plant Molecular Biology 35:509-522.*
Smith et al. 2000, Nature, 407:319-320.*
Fourgoux-Nicol et al 1999, Plant Molecular Biology 40 :857-872.*
Thomas et al. 2001, The Plant Journal 25(4):419-425.*
Colliver et al. 1997, Plant Molecular Biology 35:509-522.*
Yibrah et al. 1993 Hereditas 118:273-280.*
"GenBank Acession DQ062153.1", Basic Local Alignment Search Tool, Oct. 1, 2005, 5 pages.
Y. Arakane, et al., "The Tribolium chitin synthase genes TcCHS1 and TcCHS2 are specialized for synthesis of epidermal cuticle and midgut peritrophic matrix", Insect Molecular Biology, 2005, pp. 453-463, vol. 14, No. 5.
James A. Baum, et al., "Control of coleopteran insect pests through RNA interference", Nature Biotechnology, Nov. 2007, pp. 1322-1326, vol. 25, No. 11.
International Search Report for PCT/BR2013/000608 dated Aug. 26, 2014 [PCT/ISA/210].
Written Opinion for PCT/BR2013/000608 dated Aug. 26, 2014 [PCT/ISA/237].

* cited by examiner

*Primary Examiner* — Li Zheng
(74) *Attorney, Agent, or Firm* — Sughrue Mion, PLLC

(57) ABSTRACT

The present invention relates to the control of infestation of pests by inhibiting or reducing the expression of genes of the family of chitin synthase. The invention further provides methods and compositions for controlling pests by feeding them with one or more double-stranded RNA molecules provides by the present invention. The invention further describes a method of obtaining transgenic plants that express double-stranded RNA molecules. The present invention is preferably used for cotton-plants.

31 Claims, 6 Drawing Sheets
(5 of 6 Drawing Sheet(s) Filed in Color)
Specification includes a Sequence Listing.

A

B

METHOD AND COMPOSITIONS FOR THE GENETIC CONTROL OF INSECT PESTS IN COTTON PLANTS BY CHITIN SYNTHASE GENE SILENCING

FIELD OF THE INVENTION

The present invention relates to the field of insect pest control that attack crops, especially cotton plants, by silencing chitin synthase genes through mediation of double-stranded RNA (dsRNA) expressed in cotton plants.

BACKGROUND OF THE INVENTION

Agriculture is one of the main pillars of the economy of developing countries. In Brazil, the main crops produced are: soybeans, cotton, maize, beans, coffee beans, sugarcane, among others. However, the production of most of these crops is impaired by the incidence of insect pests and diseases. The losses in the agricultural production, caused by insect pests reach high levels of over 37%, and it is known that about 200 plant diseases are caused by phytopathogens (HAQ, S. K., et al, Protein proteinase inhibitor genes in combat against insects, pests, and pathogens: natural and engineered phytoprotection. Archives of biochemistry and biophysics, v. 431 No. 1, p. 145-159; 2004). The need to control pest insects and pathogens ion agriculture has pushed the development of different pesticides, which decrease losses and contribute to the agribusiness. However, such pesticides are highly toxic, not only to the target species, but also to other animals and even to humans.

Cotton plant is, among all the domestic and cultivatable plants, one of the most widely attacked by diseases and pest insects, besides exhibiting high sensitivity to the occurrence imposed by weeds (Beltrão, E. M., Souza, J. G. O agronegócio do algodão no Brasil. Embrapa: Brasília, v. 01, 1999). Among the main pest insects, the "bicudo-do-algodoeiro" or boll weevil (*Anthonomus grandis*) stands out—(Boheman, C. H. Description of new species. In Schoenherr, Genera et species *Curculionidum cum synonymia hujus* Familiae, vol. 7, pt. 2. Paris: Roret. 461 p., 1843), which is considered one of the most serious pests in cotton cultivation and is widespread in Mexico, Cuba, Haiti, Venezuela, Colombia, Paraguay and Brazil. This insect uses the flower buds and fruits of its host as a source of food and development site, directly impairing the commercialization of cotton fiber. The infestation levels rise rapidly, and the damages may reach 100% of the production, if control measures are not adequate. This insect represents a great potential of damage, being considered a key-pest in the planning and control of insects that are harmful to the crop, chiefly due to the difficulty of control by chemical insecticides.

Cotton plant and its pests co-exist for a long period of evolution. Plant and insect form an interdependent and competitive morphologic and biochemical system, resulting, in most cases, ion the use of part of the plant by the insect. This part used represents the damage caused by the insect to the plant and depends on the population of the pest, as well as on the capability of the plant to resist the attack and to recover from the damage undergone (Beltrão, E. M., Souza, J. G. O agronegócio do algodão no Brasil. Embrapa: Brasília, v. 01, 1999).

The plant-insect interaction can be viewed in at least two ways: from the point of view of the insect, with the plant varying from adequate to completely inadequate as a host and, on the other hand, from the point of view of the plant, where the smaller the number of species and abundance of insects associated thereto, and the smaller the effect which these insects exert on them, the greater the resistance to these insects (Santos, W. J. Identificação, biologia, amostragem e controle das pragas do algodoeiro. In: Embrapa Agropecuária Oeste; Embrapa Algodão. Algodão: tecnologia de produção, p. 296-2002).

Between one extreme and the other of resistance of the plants to pest insects, there is a complex and extensive arsenal of mechanisms of attack and counterattack to the action of the insects, which goes from a simple morphologic impediment to complex phytochemical components that interfere directly with the metabolic process involved in using the plant as a host for the insect. In practical terms, the resistance of the cotton plant to pest insects represents the capability of certain cultivars to produce cotton of better quality in larger quantity that other cultivars under attack of the same population of pest insects (Freire, E. C. Cultivares e produção de semente na melhoria da qualidade do algodão no nordeste e centro-oeste do Brasil, Boletim informative Embrapa/CNPA, 1997).

At present, there is a need to develop more selective methods, without action on the environment, which are non-persistent, biodegradable and adapt well to insect pest control programs.

Due to the dangers associated to chemical control of insects, a number of molecular approaches for the control of pests on plants have been developed. Over the past thirty years the use of *Bacillus thuringiensis* has proved to be a safe alternative, and its endotoxins are more and more transferred to commercial varieties. Fields planted with transgenic varieties exhibit a drastic reduction in the use of insecticides all over the world, which additionally causes a decrease in the cases of poisoning and also an increase in the number of beneficial insects in the plantations.

At present, the interfering RNA is a tool with great potential for combating pest insects, in view of its specificity and high efficiency in suppressing the target mRNA.

The interference RNA mechanism (RNAi) is a phenomenon that occurs naturally in the cells and in various eukaryotic organisms. Such a process, described primarily on plants, was called post-transcriptional gene silencing, or PTGS (NAPOLI, C. et al, Introduction of a Chimeric Chalcone Synthase Gene into Petunia Results in Reversible Co-Suppression of Homologous Genes in Trans. Plant Cell, V. 2, 4. p. 279-289, 1990). However, the first description of genic silencing on animals, as well as the better understanding thereof, was obtained on *Caenorhabditis elegans*, free-life nematode and model organism (FIRE, A. et al, Potent and specific genetic interference by double-stranded RNA in *Caenorhabditis elegans*. Nature, v. 391, n. 6669, p 806-811, 1998). At present, it is known that this process participates integrally in the regulation of the genic expression on various plants and other eukaryotes (LILLEY, C. J., et al, Recent progress in the development of RNA interference for plant parasitic nematodes. Molecular Plant Pathology, v. 8, n5. P. 701-711, 2007).

The action mechanism thereof is based chiefly on the introduction of a double-stranded RNA into a target organism, by micro injection or ingestion (FIRE, A., et al., Potent and specific genetic interference by double-stranded RNA in *Caenorhabditis elegans*. Nature, v. 391, n. 6669. p. 806-811. 1998). This double-stranded RNA initiates a post-transcriptional genic silencing process, through degradation of homologous mRNAs, causing a decrease in the synthesis of the corresponding protein (MEISTER, G.; TUSCHL, T., Mechanisms of gene silencing by double-stranded RNA.

Nature, v. 431, n. 7006. p. 343-349. 2004), making the survival difficult or even leads the parasite to death.

Ever since its initial description, this technique has become a valuable tool for the functional genomics of insects, in particular in the study of the genic function on *Drosophila melanogaster* (MESQUITTA, L.; PATERSON, B. M., Targeted disruption of gene function in *Drosophila* by RNA interference (RNA-i): a role for nautilus in embryonic somatic muscle formation. Proc Natl Acad Sci USA, v. 96, n. 4. p. 1451-1456. 1999; KENNERDELL, J. R.; CARTHEW, R. W., Heritable gene silencing in *Drosophila* using double-stranded RNA. Nat Biotechnol, v. 18, n. 8. p. 896-898. 2000). Recent Works showed the feasibility of plants that used to produce dsRNA in resistance against pest insects. These transgenic plants produced specific dsRNA against essential genes in the digestive tract of the insects, causing mortality in 24 hours after contact with the RNAi (BAUM, J. A., et al., Control of coleopteran insect pests through RNA interference. Nat Biotechnol, v. 25, n. 11. p. 1322-1326. 2007; MAO, Y. B., et al., Silencing a cotton bollworm P450 monooxygenase gene by plant mediated RNAi impairs larval tolerance of gossypol. Nat Biotechnol, v. 25, n. 11. p. 1307-1313. 2007).

The application of RNAi in planta has a great potential as an approach to handling insects. The specificity of the RNAi for insecticidal purposes is an important consideration for the use of this technology in practical applications, since the effects on non-target insects may be minimized. Among other advantages, this technique enables the use of only sequence fragments, since the translation of a protein is not necessary, which minimizes the worries about biosafety and allergenicity, and represents a probably more effective form of control than the present-day ones.

Chitin, a linear polysaccharide formed by residues of N-acetyl-D-glycosamine United by β (1-4) links, is widespread among insects, which use this versatile biopolymer in various anatomic structures. Two main extracellular structures where the deposition of chitin takes place are the cuticle that covers the epidermis and the peritrophic membrane that covers the middle intestine (MUTHUKRISHNAN, S., et al., Chitin Metabolism in Insects. In Insect Molecular Biology and Biochemistry, 1 ed.; Gilbert, L. I., Ed. Elsevier: London, pp. 193-225. 2012).

The peritrophic membrane is a functional structure that covers the middle intestine of the insects. The main functions attributed to this membrane are that of mechanical protection against injury to cells of the middle intestine (WIGGLESWORTH, V., The principles of insect physiology. 7 ed.; Chapman and Hall: London, Vol. p 827. 1972), a physical barrier against microorganisms (PETERS, W., Peritrophic membranes. Springer-Verlag New York, Vol. 1992), a barrier selective for digestive enzymes and digestion products (DAY, M. F.; WATERHOUSE, D. F., Functions of the alimentary system. John Wiley: New York, Vol. p 299-310. 1953) and actuation as a mechanism of recycling digestive enzymes, a phenomenon known as ectoendoperitrophic circulation (TERRA, W. R., Physiology and Biochemistry of Insect Digestion—an Evolutionary Perspective. Brazilian Journal of Medical and Biological Research, v. 21, n. 4. p. 675-734. 1988; TERRA, W. R.; FERREIRA, C., Insect Digestive Enzymes—Properties, Compartmentalization and Function. Comparative Biochemistry and Physiology Biochemistry & Molecular Biology, v. 109, n. 1. p. 1-62. 1994; TERRA, W. R., The origin and functions of the insect peritrophic membrane and peritrophic gel. Archives of Insect Biochemistry and Physiology, v. 47, n. 2. p. 47-61, 2001).

The insect cuticle or exoskeleton is a multifunctional structure that serves as a physical support, and also gives its shape, enables displacement, imparts impermeability to the body, and a number of localized mechanic specializations, such as high degree of adhesion, resistance to wear and diffusion control. In this structure, its mechanical properties are attributed to its main constituent, chitin (VINCENT, J. F., et al., Design and mechanical properties of insect cuticle. Arthropod Struct Dev, v. 33, n. 3. p. 187-199. 2004).

The synthesis and deposition of chitin on the cuticle and on the peritrophic membrane comprise a sequential series of complex biochemical, biophysical, intracellular and extracellular transformations, some of which still little understood (MOUSSIAN, B., et al., Assembly of the *Drosophila* larval exoskeleton requires controlled secretion and shaping of the apical plasma membrane. Matrix Biol, v. 26, n. 5. p. 337-347. 2007). Since chitin is absent in plants and vertebrates, its biosynthetic pathway is one of the main targets for the development of insecticides ever since 1970 (VERLOOP, A., et al., Benzoylphenyl Ureas—A New Group of Larvicides Interfering with Chitin Deposition. In Pesticide Chemistry in the 20th Century, AMERICAN CHEMICAL SOCIETY: Vol. 37, pp. 237-270. 1977). Among the enzymes involved in the synthesis of chitin on insects, a special approach has been given to the last step of the pathway, which is measured by the enzyme chitin synthase (EC 2.4.1.16), which catalyzes the polymerization of chitin from activated monomers of UDP-N-acetilglicosamina (MERZENDORFER, H., The cellular basis of chitin synthesis in fungi and insects: common principles and differences. Eur J Cell Biol, v. 90, n. 9. p. 759-769. 2011).

The interruption or the decrease in the synthesis of enzymes that participate in the biosynthesis of constituents of the cuticle and of the peritrophic membrane of the insect by means of the RNAi technology proves to be a specific form of control of pest insects.

Chitin synthase A (or type 1) on insects is the main enzyme involved in the biosynthesis of chitin of the cuticle and of the trachea. However, chitin synthase B (or type 2) on insects is the main enzyme involved in the biosynthesis of chitin of the peritrophic membrane, both chitins synthases of insects have been studied as ideal targets for the development of strategies of control of pest insects.

In the present invention, one shows the insecticidal effect of dsRNA molecules on the "bicudo-do-algodoeiro" or boll weevil (*Anthronomus grandis*), the main pest of cotton-plantation in Brazil. The insecticidal effect is attributed to the inhibition of the transcript levels of the enzymes chitin synthase 1 and 2, which caused damages to the development of eggs and adults of *A. grandis* when subjected to the dsRNA treatment against these enzymes.

SUMMARY OF THE INVENTION

The present invention relates to a method for reducing or inhibiting the expression of genes involved in the biosynthesis of chitin in eukaryotic cells, particularly in animal cells, resulting in the death, inhibition, atrophy or interruption of feeding of a target pest.

In an embodiment, the invention describes nucleic acid molecules substantially similar to the sequences selected from the group consisting of SEQ ID No 1, SEQ ID No 2, SEQ ID No 3, SEQ ID No 4, SEQ ID No 5 and SEQ ID No 6 or fragments or complements thereof. The invention describes dsRNA molecules from the sequences selected from the group consisting of SEQ ID No 1, SEQ ID No 2, SEQ ID No 3, SEQ ID No 4, SEQ ID No 5 and SEQ ID No 6, or fragments or complements thereof, stabilized or the expression of one or more microRNAs (miRNA) or siRNAs for inhibition of the expression of a target-gene, in coleopteran pest, expressed from this sequences and fragments thereof.

The invention further describes compositions containing nucleic acid substantially similar to the sequences selected from the group consisting of SEQ ID No 1, SEQ ID No 2, SEQ ID No 3, SEQ ID No 4, SEQ ID No 5 and SEQ ID No 6, or fragments or complements thereof, for the control of pest insects, particularly the “bicudo-do-algodoeiro” or boll weevil (*Anthonomus grandis*).

The also relates to a method for suppressing genic expression on a coleopteron pest, such as the “bicudo-do-algodoeiro” or boll weevil, or a related species, which comprises the step of supplying in the diet of the pest a gene suppressing amount, relying on at least one dsRNA molecule, transcribed from a nucleotide sequence substantially similar to the sequences selected from the group consisting of SEQ ID No 1, SEQ ID No 2, SEQ ID No 3, SEQ ID No 4, SEQ ID No 5 and SEQ ID No 6, or fragments or complements thereof, which has at least one complementary fragment of a sequence of the mRNA inside the pest cells.

The invention has also the aspects of chimeric genes, genic constructs containing the nucleic acid molecules of the present invention, vectors of transformation and expression, transgenic cells and organism, methods for the expression of the molecule of the present invention in transgenic organism, as well as the use thereof in controlling pests. The invention also comprises a method for obtaining a transgenic plant by using the genic constructs of the present invention and a method of producing food, which comprises obtaining a plant transformed with polynucleotide containing a nucleotide sequence substantially similar to the sequences selected from the group consisting of SEQ ID No 1, SEQ ID No 2, SEQ ID No 3, SEQ ID No 4, SEQ ID No 5 and SEQ ID No 6, or fragments or complements thereof, and the preparation of food from said plant or a part thereof.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

Figure 1:
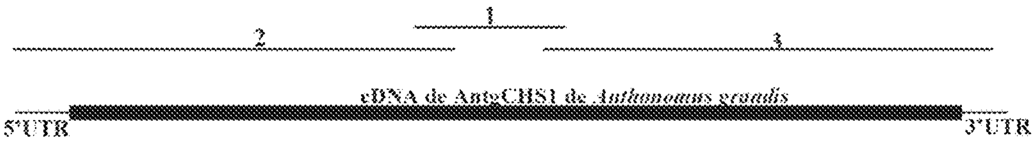
FIG. 1—Strategy of cloning the cDNA of AntgCHS1. The complete sequence of the cDNA of AntgCHS1 was determined by overlapping 3 PCR fragments.

The present invention describes methods and compositions for controlling pests, especially cotton-plant pests. For instance, the present invention provides recombinant DNA technologies for repressing or inhibiting post-transcriptionally the expression of a target sequence in the cell of a pest. This effect is achieved by feeding to one or more pests double-strain RNA or fragments of RNA (miRNA) or siRNA) transcribed from the whole target coding sequence of from a part thereof, thus controlling the infestation. As a result, the present invention relates to specific sequences of inhibition of the expression of coding sequences, using double-strain RNA (dsRNA), including little interfering RNA (siRNA), to achieve the desired levels of pest control.

The present invention provides a method of inhibiting the expression of a target gene in coleoptera. In certain embodiments, the method comprises modulating or inhibiting the expression of one or more target-gene of coleoptera that brings about the inhibition of development, reproduction and/infectivity and possibly results in death of the insect. More specifically, the present invention relates to inhibition of the genes of the family of chitin synthase ion coleoptera, resulting in the interruption of the development and malformation of insects, both larvae and adults, and may result in death of the insect. The method comprises introducing double-stranded RNA (dsRNA) in a partial manner, stabilizing, including the modified forms thereof, such as small interfering RNA sequence (siRNA), in the cells or in an extracellular medium, such as the middle intestine, within coleoptera in which the dsRNA gets into the cell and inhibits the expression of at least one or mare target genes, and where the inhibition exerts a deleterious effect on the pest. The methods and the associated compositions can be used for limiting or eliminating the infestation of coleoptera or any pest host, symbiont pest, or environment in which the pest is present through one or more compositions that comprise the dsRNA molecule described herein in the diet of the pests.

The present invention further provides examples of nucleic acid compositions that are homologous to at least one portion of the sequences selected from the group consisting SEQ ID No 1, SEQ ID No 2, SEQ ID No 3 and SEQ ID No 4, SEQ ID No 5 and SEQ ID No 6, or fragments or complements thereof. A specific example of such nucleic acids provided by the invention is described in the SEQ ID NO 2 e SEQ ID NO 6 or complements thereof.

In a further embodiment, the invention provides a method for suppressing the expression of the gene of a coleopteran pest, such as "bicudo-do-algodoeiro" (boll weevil) or of related species, which comprises the step of providing, in the diet of the pest, a gene suppressing amount of at least one dsRNA molecule transcribed from a nucleotide sequence, such as described herein, at least one segment of which is complementary to a miRNA sequence in the cell of the pest. The method further comprises death, dwarfishness, or cessation of feeding of the pest. A dsRNA molecule, including its modified form such as a siRNA molecule, fed to a pest according to the invention, may be of at least about 80, 81, 82, 83, 84, 85, 86, 87, 88 89, 90, 91, 92, 93, 94, 95, 96, 97, 98, 99, or about 100% of identity with an RNA molecule transcribed from the sequences selected from the group consisting of SEQ ID No 1, SEQ ID No 2, SEQ ID No 3 e SEQ ID No 4, SEQ ID No 5 and SEQ ID No 6, or fragments or complements thereof.

The present invention further provides a stabilized dsRNA molecule or the expression of one or more MiRNAs for inhibition of the expression of a target gene in a coleopteran pest expressed from this sequence and the fragments thereof. A stabilized sRNA, including an siRNA, miRNA molecule, or comprising at least two coding sequences that are arranged in one sense and the antisense orientation with respect to at least one promoter, wherein the nucleotide sequence that comprises a chain with sense and an antisense one is related or linked by a spacing sequence of at least from about thereto about ten Thousand nucleotides, wherein the chain with sense and the antisense chain may be formed of different lengths, and each of the two parts encodes sequences of at least 80% of sequence identity, at least 90%, at least 95%, at least 98%, or 100% of sequence identity to any sequence of one or more nucleotide (s) according to the sequences selected from the group consisting of SEQ ID No 1, SEQ ID No 2, SEQ ID No 3 and SEQ ID No 4, SEQ ID No 5 and SEQ ID No 6, or fragments or complements thereof.

Besides, the invention further provides a fragment or concatamer of a nucleic acid sequence selected from the group consisting of SEQ ID No 1, SEQ ID No 2, SEQ ID No 3 and SEQ ID No 4, SEQ ID No 5 and SEQ ID No 6, or fragments or complements thereof. The fragment can be defined as causing death or preventing the development of a harmful organism when expressed as a dsRNA and supplied to the pest. For instance, the fragment may comprise at least about 19, 21, 23, 25, 40, 60, 80, 100, 125 or more contiguous nucleotides of the sequences selected from the group consisting of SEQ ID No 1, SEQ ID No 2, SEQ ID No 3 e SEQ ID No 4, SEQ ID No 5 e SEQ ID No 6, or fragments or complements thereof, or one complement thereof, A beneficial DNA segment for use in the present invention is at least 19 to about 23, or about 23 to about 100 nucleotides, up to about 2000 nucleotides in length or more. Particularly useful for the present invention are the DNA sequences including about 19 to about 400 nucleotides homologous to a target sequence of pests. The invention also provides a ribonucleic acid expressed from any of such sequences, including a dsRNA. The sequence selected for use in the expression of a gene suppressing agent may be constituted from a single sequence derived from one or more target pests and intended to be used in the expression of an RNA that functions in suppressing a single gene or a family of genes in one or more target pest, or the DNA sequence may be constituted as a chimera of a plurality of DNA sequences. Specifically for the present invention, this Family of genes is related to the Family of the genes of chitin synthase, specifically to chitin synthase 1' and chitin synthase 2.

In a further embodiment, the invention provides recombinant DNA constructs comprising a nucleic acid molecule that encodes a dsRNA molecule described herein. The dsRNA may be formed by a transcription strand of the molecule of a nucleotide sequence that is at least about 80% to about 100% identical to the sequences selected from the groups consisting of SEQ ID No 1, SEQ ID No 2, SEQ ID No 3 and SEQ ID No 4, SEQ ID No 5 and SEQ ID No 6, or fragments or complements thereof. Such recombinant DNA constructs can be defined as the production of dsRNA molecules, capable of inhibiting or reducing the expression of the endogenous target gene in a pest cell after ingestion. The construct may include a nucleotide sequence of the invention operatively linked to a promoter sequence that functions in the host cell. The present invention may make use of tissue-specific or constitutive promoters. Preferably for the present invention, the tissue-specific promoters may be, but are not limited to promoters specific for flower buds of cotton plants.

Nucleic acid constructs according to the invention may comprise at least one nucleotide sequence that does not occur naturally and that may be transcribed in single-strand RNA, capable of forming a dsRNA molecule in vivo by hybridization. Such dsRNA sequences may be supplied to the diet of a coleopteran pest to achieve the desired inhibition. Preferably for the present invention the dsRNA molecule is formed by nucleotide sequences substantially similar to the sequences selected from the group consisting of SEQ ID No 1, SEQ ID No 2, SEQ ID No 3 and SEQ ID No 4, SEQ ID No 5 and SEQ ID No 6, or fragments or complements thereof.

A recombinant DNA sequence may contain sequences substantially similar to the sequences selected from the group consisting of SEQ ID No 1, SEQ ID No 2, SEQ ID No 3 and SEQ ID No 4, SEQ ID No 5 and SEQ ID No 6, or fragments or complements thereof. The dsRNAs may either express from constructs introduced into various different transformation events, or may be introduced into a single nucleic acid molecule. The dsRNAs may be expressed by using a single promoter or multiple promoters. In an embodiment, the invention enables a recombinant host cell to have in its genome at least one recombinant DNA sequence that is transcribed to produce at least one dsRNA molecule, which functions when ingested by a coleopteran pest to inhibit or reduce the expression of a target gene in a pest. The dsRNA molecule may be encoded by the sequences selected from the group consisting of SEQ ID No 1, SEQ ID No 2, SEQ ID No 3 and SEQ ID No 4, SEQ ID No 5 and SEQ ID No 6, or fragments or complements thereof. The present invention also provides a transformed plant cell having in its genome at least one recombinant DNA sequence described herein. The transgenic plants that comprise such a transformed plant cell are also provided, including the progeny plants of any generation, seeds, and plant products, each comprising the recombinant DNA.

The methods and compositions of the present invention may be applied to any monocotyledonous and dicotyledonous plant, depending on the desired control of coleopteran pests. Thus, the present invention describes a transformed plant with a recombinant DNA sequence, as described in the sequences selected from the group consisting of SEQ ID No 1, SEQ ID No 2, SEQ ID No 3 and SEQ ID No 4, SEQ ID No 5 and SEQ ID No 6, fragments or concatamers or complements thereof, which is transcribed to produce at least one dsRNA molecule, which functions when ingested by a coleopteran pest to inhibit or reduce the expression of a target gene.

The invention also provides combinations of methods and compositions for controlling infestations of coleopteran pests. One way of providing a dsRNA method as described herein for protection of plants against infestations of insects is in conjunction with one or more insecticidal agents that exhibit characteristics other than those exhibited by the dsRNA methods and compositions. For instance, one or more Bt proteins may be supplied to the diet of the pests of insects, in combination with one or more dsRNA, as described herein. The composition formulated for topical application or derived, using a transgenic approach, which combines the methods and the dsRNA combinations with Bt can be used for creating synergisms that were not known before in the art to control infestation of insects. One synergism is the reduction in the level of expression necessary to the dsRNA (s) or the Bt protein (s). When combined, the smallest effective dose of each of the agents for controlling pests may be used. One believes that the insecticidal Bt protein creates entrance pores, through which the dsRNA molecules are capable of penetrating more effectively the spaces away from the intestine of the pest of insects, or more effectively for cells in proximity of injuries created by the Bt protein, thus requiring smaller amount of Bt or dsRNA to achieve the desired result of insecticidal action or desired inhibition or suppression of a specific biologic function on the target pest.

Therefore, the present invention provides a composition containing two or more different pesticidal agents that are toxic to the same pest or species of insects, wherein at least one of which comprises one dsRNA described herein. In certain embodiments, the second agent may be one selected from the group consisting of a patatin, an insecticidal protein of *Bacillus thuringiensis*, an insecticidal *Xenorhabdus* protein, an insecticidal *Photorhabdus* protein, an insecticidal *Bacillus laterosporous*, an insecticidal *Bacillus sphaericus*, enzymes of the family of chitinase and a lignin. An insecticidal *Bacillus thuringiensis* protein may be any one of a number of insecticidal proteins, including, but not limited to Cryl, Cry8, Cry10, Cry35 TIC851, CryET70, Cry225 TIC901, TIC1201, TIC407, TIC417, insecticidal protein CryET33 and binary CryET34, insecticidal binary protein CryET80 and CryET76, binary insecticidal protein TICIOO and TICIOI, insecticidal binary of protein PS 14961, insecticidal VIP protein, protein TIC900 or the like, or combinations of insecticidal proteins ET29 or ET37 with insecticidal proteins TIC810 or TIC812 and insecticidal chimeras of any of the proteins cited before.

A ribonucleic acid that is supplied to the diet may be provided in an artificial diet formulated to meet the special nutritional needs for a determined pest. The may also be a transformed recombinant cell with a DNA sequence constructed for expression of the target agent, the RNA or the gene suppression agent. After injection of one or more cells transformed by the pest, the desired result is phenotypically observed, indicating that the agent was used for inhibiting or reducing the expression of a target nucleotide sequence that is inside the pest cells.

A target gene can encode for suppressing an essential protein. For the present invention, the target gene is of the family of chitin synthase, the function of which is to constitute the cuticle, trachea, and chitin of the peritrophic membrane. Therefore, the inhibition or reduction of the expression of such a gene may affect essential functions for survival of the insect to be selected from the group of differentiation and development of the cuticle, formation of the egg, larval maturation, larval stage transition, purgation, digestion and assimilation of nutrients, protection against pathogens.

Another aspect of the present invention is to provide a method for improving the yield of a plant subjected to infestation of pests of insects, which comprises the steps of: a) introducing a polynucleotide comprising a sequence substantially similar to the sequences selected from the group consisting of SEQ ID No 1, SEQ ID No 2, SEQ ID No 3 and SEQ ID No 4, SEQ ID No 5 and SEQ ID No 6, or fragments or complements of these or concatamers in said plant, and b) cultivating the plant so as to enable expression of said characteristic. Commerce A further aspect of the invention is to provide products that are agronomically and commercially important and/or matter compositions, including, but not limited to livestock feed, base products, products and by-products that are intended to be used as food for human consumption or for use in the compositions, and products that are intended for human consumption, including, but not limited to cottonseed meal, cottonseed oil, cottonseed cakes, cotton feather, cotton fiber, cereals, and so on. Such compositions can be defined as containing a detectable amount of a nucleotide sequence established herein, and to they are also diagnose for any transgenic happening containing such nucleotide sequences. These products are useful at least because they are susceptible to being obtained from crops propagated with less organophosphated pesticides and, as a result, from the incorporation of the nucleotides of the present invention for controlling infestation of pests and coleoptera on plants. Such base goods and products can be produced from seeds produced from a transgenic plant, wherein the plant expresses RNA from one or more contiguous nucleotides of the present invention or nucleotides of one or more coleopteran pests and respective complements.

A method of making a product of this type comprises obtaining a plant transformed with a polynucleotide comprising a sequence selected from the group consisting of SEQ ID No 1, SEQ ID No 2, SEQ ID No 3 and SEQ ID No 4, SEQ ID No 5 and SEQ ID No 6, or fragments or complements thereof, or concatamers thereof, and preparation of a base product from the plant or a part thereof, is also provided in the present invention. Besides, a method of producing human food or animal feed, which comprises obtaining a plant transformed with a polynucleotide comprising a sequence selected from the group consisting of SEQ ID No 1, SEQ ID No 2, SEQ ID No 3 and SEQ ID No 4, SEQ ID No 5 and SEQ ID No 6, or fragments or complements thereof, or concatamers thereof, and preparing the food or animal feed from said plant or a parte thereof is a further aspect of the invention.

The invention also provides a means readable by computer, which has a registered sequence selected from the group consisting of SEQ ID No 1, SEQ ID No 2, SEQ ID No 3 and SEQ ID No 4, SEQ ID No 5 and SEQ ID No 6, or fragments or complements thereof, or concatamer thereof, for use in a certain number of computer applications, including, but not limited to the DNA identity and search for similarity, identity and search of similarity of protein, characterizations of profiles of transcription, comparisons between genomes, and analysis of artificial hybridizing.

In the context of this description, numberless terms will be used, and so they are better detailed hereinafter.

The term "nucleic acid" refers to a big molecule, which may be a single strand or a double strand, composed of monomers (nucleotides), containing a sugar, a phosphate and a purine base or pyrimidine base. A "nucleic acid fragment" is a fraction of a given nucleic acid molecule. "Complementarity" refers to the specific pairing of purine and pyrimidine bases consisting of nucleic acids: pairs of adenine with thymine and pairs of guanine with cytosine. Then, the "complement" of a first nucleic acid fragment is complementary to the first nucleotide sequence.

On more developed plants, deoxyribonucleic acid (DNA) is the genetic material, while ribonucleic acid (RNA) is involved in the transfer of the DNA information in proteins. A "genome" is the whole main part of the genetic material contained in a cell of an organism. The term "nucleotide sequence" refers to the nucleotide polymer sequences, forming a DNA or RNA strand, which may be single or double strand, optionally synthetics, non-natural or with altered nucleotide bases capable of incorporation into DNA or RNA polymers. The term "oligomer" refers to short nucleotide sequences, usually up to 100 bases in length. The term "homologous" to the link between the sequences of nucleotides having two nucleic acid molecules or between the sequences of amino acids of two protein molecules. The estimate of such homology is provided hybridizing DNA-DNA or RNA-RNA under stringency conditions as defined in the prior art (as mentioned in document US20030074685, Hames and Higgins, Ed. (1985) Nucleic Acid Hybridization, IRL Press, Oxford, U.K.); or by the comparison of similarity of sequences between two nucleic acid or protein molecules (as mentioned in document US20030074685, Needleman et al, J. Mol. Biol. (1970) 48:443-453).

"Gene" refers to the nucleotide fragment that expresses a specific protein, including preceding regulatory sequences (non-translated region 5') and following ones (non-translated region 3') with respect to the coding region. "Native gene" refers to an isolated gene with its own regulatory sequence found in nature. "Chimeric gene" refers to the gene that comprises coding, regulatory and heterogeneous sequences not found in nature. The chimeric gene of the present invention comprises isolated nucleic acid molecules, in the sense or antisense orientation, linked operatively to active promoters. Genic constructs of the present invention may contain 1 or more chimeric genes and may or may not exhibit introns. "Endogenous gene" refers to the native gene usually found in its natural location in the genome and is not isolated. An "exogenous gene" refers to a gene that is not normally found in the host organism, but which is introduced by genic transfer. "Pseudogene" refers to a nucleotide sequence that does note code a functional enzyme.

"Coding sequence" refers to the DNA sequence that codes a specific protein and excludes the non-coding sequence. An "interrupted coding sequence" means the sequence that acts as separator (for instance, one or more introns linked by junctions). An "intron" is a nucleotide sequence that is transcribed and the re-linkage of the mRNA within the cell, generating a mature mRNA that con be translated in a protein. Examples of introns include, but are not limited to intron pdk2, intron catalase of castor bean, intron Delta 12 desnaturase of cotton, Delta 12 desnaturase of *Arabidopsis*, intron ubiquitin of maize, intron of SV40, introns of the gene of malate synthase.

"RNA transcript" refers to the product resulting from transcription catalyzed by RNA polymerase of a DNA sequence. When the RNA transcript is a perfect copy of the DNA sequence, it is referred to as being a primary transcript or it may be an RNA sequence derived from a post-transcriptional process of the primary transcript and is then referred to as being a mature transcript. "Messenger RNA" (mRNA)" refers to the RNA that is without introns. "Sense RNA" refers to an RNA transcript that includes the mRNA. "Antisense RNA" refers to an RNA transcript that is complementary to all the parts of a primary transcript or mRNA and that can block the expression of a target gene through interference with the processing, transportation and/or translation of its primary transcript of mRNA. The complementarity of an antisense RNA may be any part of the specific genic transcript, that is, non-translated sequence 5', non-translated sequence 3', introns or coding sequence. Besides, the antisense RNA may contain ribozyme sequence regions that enhance the efficacy of the antisense RNA to block the genic expression. "Ribozyme" refers to the catalytic RNA and includes specific endoribonuclease sequences. "DsRNA (double strain)" refers to the clamp structure formed between the sequence of the mRNA or sense RNA, the sequence of a spacing region and the sequence of the antisense RNA. "Spacing region" refers to the nucleotide sequence that is not related to the sequence of the target gene, as a sequence of an intron.

The term "vector" refers to a replicon, as a plasmid, phages or virus, in which other genic sequences or elements (be they of DNA or RNA) may be linked. Thus, the genes may be replicated together with the vector. Preferably, one of the vectors of interest of the present invention refers to phagemid. The term "phagemid" refers to a vector that contains sequence for replication in phage and in bacterium. This vector has characteristics that meet the specifications of the host cell, as well as selecting and promoting agents. The term "recombinant vector" results from the combination of a commercial vector with nucleic acid molecules of the present invention, operatively linked to a promoter of interest and a termination signal. Such vectors can be obtained commercially, including those supplied by Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). A few examples of vectors used in the present invention, but not limited thereto, are the vectors of the series pCambia (BioForge Co.), pB1121 (Chen, Po-Yen; Wang, Chen-Kuen; Soong, Shaw-Ching; To, Kin-Ying. Complete sequence of the binary vector pB1121 and its application in cloning T-DNA insertion from transgenic plants. *Molecular Breeding* vol. 11 issue 4 May 2003. p. 287-293), pBSK (Addgene Co.), pGEM-T easy (Promega Corporation), pET101/D-TOPO (Invitrogen). The obtainment of recombinant vectors comprising promoters linked to nucleic acids is known in the art and can be found in Sambrook et al. (Sambrook, J., Russell, D. W., Molecular Cloning, A Laboratory Manual, 2nd ed., Cold Spring Harbor Laboratory Press. 1989).

"Substantially similar" or "substantial similarity" refers to fragments of nucleic acids in which changes in one or more nucleotide bases do not prevent the capability of the nucleic acid fragment from mediating the alteration of the gene expression by gene silencing through, for instance, the antisense technology, co-suppression or interference RNA (iRNA/RNAi). Substantially similar nucleic acid fragments of the present invention may also be characterized by the percentage of similarity of their nucleotide sequences with the nucleotide sequences of the nucleic acid fragments described herein (SEQ ID No 1, SEQ ID No 2, SEQ ID No 3 and SEQ ID No 4, SEQ ID No 5 and SEQ ID No 6), as determined by a few common algorithms employed in the prior art. The preferred nucleic acid fragments are those whose nucleotide sequences have at least about 40 or 45% of sequence identity, preferably about 50% or 55% sequence identity, more preferably about 60 or 65% sequence identity, more preferably about 70% or 75% sequence identity, more preferably about 80% or 85% sequence identity, still more preferably about 90%, 91%, 92%, 93%, 94%, 95%, 96%, 97%, 98%, or 99% sequence identity as compared to the reference sequence.

One of the ways to form the dsRNA is that the nucleotide sequence of the target gene in the sense orientation, as well as a nucleotide sequence in the antisense orientation should be present in the DNA molecule, and there may or may not be a spacing region between the sense and antisense nucleotide sequences. The mentioned nucleotide sequences may be constituted by about 19 nt to 2000 nt or even about 5000 nucleotides or more, each having a total substantial sequence similarity with about 40% to 100%. The longer the sequence, the less stringency is required for total substantial sequence similarity. The fragments containing at least about 19 nucleotides should have preferably about 90%, 91%, 92%, 93%, 94%, 95%, 96%, 97%, 98%, or 99% sequence identity as compared to the reference sequence, with the possibility of having about 2 non-contiguous different nucleotides. Preferably, one uses fragments above 60 pb, more preferably fragments between 100 and 600 pb.

In one of the aspects of the invention, the dsRNA molecule may comprise one or more regions having a substantial sequence similarity for the regions with at least about 19 consecutive nucleotides of the sense nucleotides of the target gene, defined as first region and one or more regions having a substantial sequence similarity for the regions with about 19 consecutive nucleotides of the complement of the sense nucleotides of the target gene, defined as second region, wherein these regions may have pairs of bases separating them from each other.

Conveniently, the dsRNA (double-stranded DNA) as described may be introduced into host cells by introducing and possibly integrating a gene construct containing the nucleic acid molecules of the present invention, transcription thereof for the production of the dsRNA. Therefore, in another embodiment the invention is also supported by having a gene construct that is capable of being expressed in eukaryotic organisms of interest, operatively linked to a DNA molecule that, when transcribed, produces a dsRNA molecule comprising a first region and a second region, wherein:

(a) the first region comprises a nucleotide sequence of at least about 19 consecutive nucleotides having a substantial sequence similarity with at least about 19 consecutive nucleotides of the sequence of sense nucleotides of the target gene.

(b) the second region comprises a nucleotide sequence of about at least 19 consecutive nucleotides having a substantial sequence similarity with the complement of about at least 19 consecutive nucleotides of the sequence of sense nucleotides of the target gene;

(c) the first and the second regions are capable of forming a double-stranded RNA region, which may have, in addition to the total length of the first and of the second regions, a spacing region between them containing at least about 3 nucleotides.

"Promoter" refers to the DNA sequence in a gene, usually located upstream of the coding sequence, which controls the expression of the coding sequence, promoting the recognizance of the RNA polymerase sequence and other factors required for the transcription itself. In an artificial DNA construct, promoters may also be used for transcribing dsRNA. Promoters may also contain DNA sequences that are involved in linking protein factors which control the effect of the transcription start in response to physiologic conditions or development conditions.

In one of the aspects of the invention, the promoter is a constitutive promoter. In another aspect of the invention, the activity of the promoter is stimulated by external or internal factors such as, but not limited to hormones, chemical compounds, mechanical impulses, and conditions of biotic or abiotic stress. The activity of the promoter may also be regulated in a temporal and special manner (as for instance, tissue-specific promoters and promoters regulated during the development).

The promoter may contain "enhancers" elements. An enhancer is a DNA sequence that can stimulate promoter activity. It may be an innate element of the promoter or a heterologous element inserted for raising the level and/or the tissue-specificity of a promoter. "Consecutive promoters" refer to those that direct the gene expression in all of the tissues and all the time. "Tissue-specific promoters" or "development-specific" promoters are those that direct the gene expression almost exclusively in specific tissues, such as leaves, roots, stems, flowers, fruits or seeds, or in specific development stages in a tissue, as in the beginning or in the end of embryogenesis. The term "Expression" refers to the transcription and stable accumulation of the dsRNA derived from the nucleic acid fragments of the present invention, which, in conjunction of the protein production apparatus of the cell, results in altered levels of mio-inositol 1-phosphate synthase. "Inhibition by interference" refers to the production of dsRNA transcripts capable of preventing the expression of the target protein.

"Suitable regulatory sequences" refer to the nucleotide sequences in native or chimeric genes that are located above (non-translated region 5'), within, and/or below (non-translated region 3') of the nucleic acid fragments of the invention, which control the expression of the nucleic acid fragments of the invention.

"Altered levels" refer to the production of gene products in transgenic organisms in amounts or proportions that differ from those in normal or non-transgenic organisms. The present invention also reports vectors that include sequence of the gene of the chitin synthase 1 and 2 enzymes in sense and antisense orientation, and host cells, which are genetically engineered with vectors of the invention. "Transformation" refers to the transfer of the exogenous gene into the genome of a host organism and its genetically stable heritage.

"Plants" refer to photosynthetic organisms, both eukaryotic and prokaryotic, wherein the term "developed plants" refer to eukaryotic plants. The nucleic acids of the invention may be used to impart desired tracts in essentially any plant. Then, the invention has use on various species of plants, including species of the genera: *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis*, Fragaria, Glycine, *Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza*, Panieum, Pannesetum, *Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna*, and *Zea.*

In one of the aspects of the invention, the promoter is a promoter expressed in plants. As used herein, the term "promoter expressed in plants" means a DNA sequence that is capable of initiating and/or controlling the transcription of a plant cell. This includes any promoter of plant origin; any promoter of non-plant origin which is capable of directing the expression. In a plant cell, for instance, promoters of viral or bacterial origin such as CaMV35S (as mentioned in patent application US20030175783, Hapster et al, 1988 Mol. Gen. Genet. 212, 182-190) and promoter of the gene present in the T-DNA of *Agrobacterium*; tissue-specific or organ-specific promoters, including, but not limited to seed-specific promoters, (WO8903887), organ-primordia-specific promoters (as mentioned in patent application US20030175783, An et al., 1996 The Plant Cell 8, 15-30), stem-specific promoters (as mentioned in patent application US20030175783, Keller et al., 1988 EMBO J. 7: 3625-3633), leaf-specific promoters (as mentioned in patent application US20030175783, Hudspeth et al., 1989 Plant Mol Biol 12:579-589), mesophyle-specific promoters, root-specific promoters (as mentioned in patent application US20030175783, Keller et al., 1989 Genes Devel. 3:1639-1646), tuber-specific promoters (as mentioned in patent application US20030175783, Keil et al., 1989 EMBO J. 8: 1323:1330), vascular-tissue-specific promoters (a mentioned in patent application US20030175783, Peleman et al., 1989 Gene 84: 359-369), stamen-specific promoters (WO8910396, WO9213956), dehiscence zone-specific promoter (WO9713865); and the like.

The termination signal of the transcription and the polyadenylation region of the present invention includes, but is not limited to SV40 termination signal, HSV TK termination signal of the gene of nopalin synthase of *Agrobacterium tumefasciens* (nos), termination signal of the gene RNA 35S do CaMV, termination signal of the virus that attacks *Trifolium* subterranean (SCSV), termination signal of the gene trpC of *Aspergillus nidulans*, and other similar ones.

The present invention also includes providing dsRNA molecules, which can be obtained by transcription of the molecules contained in the gene constructs, that which are useful for the methods according to the invention.

Another objective of the present invention is to provide eukaryotic cells, eukaryotic organisms containing dsRNA molecules of the invention, or containing the chimeric genes or the gene constructs capable of producing dsRNA molecules of the invention. The gen constructs may be stably integrated in the genome of the cells of eukaryotic organisms.

In another aspect of the invention, the gene constructs may be provided in a DNA molecule capable of replicating in an autonomous manner in the cells of eukaryotic organisms, such as viral vector. The gene construct or the dsRNA may also be arranged in a transient way in the cells of eukaryotic organisms.

The gene constructs or chimeric gene of the invention may be introduced into the genome of the desired hos plant through a number of conventional techniques. For instance, one it can be introduced directly into the genomic DNA of the plant cell by using techniques such as electroporation and microinjection of protoplasts from plant cells, or the construct may be introduced directly into the plant tissue by using ballistic methods, such as bombardment of particles covered with DNA.

Microinjection techniques are known from the prior art and are well described in the scientific and patent literature. The introduction of gene constructs by using precipitations of polyethylene glycol is described in Paszkowski et al. Embo J. 3:2717-2722, 1984 (as mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501).

Alternatively, the gene constructs may be combined with suitable flanked regions of T-DNA and introduced into host conventional vector *Agrobacterium tumefasciens*. The virulence function of the host *Agrobacterium* tumefasciens will direct the insertion of the gene constructs and adjacent marker into the DNA of the plant cell when the cell is infected by the bacterium. Transformation techniques mediated by *Agrobacterium* tumefasciens, including disarmament and the use of binary vectors, are well described in the scientific literature (as mentioned in patent application US 20020152501, Horsch et al. Science 233:496-498, 1984; and Fraley et al. Proc. Natl. Acad. Sci. USA 80:4803, 1983).

Cells of transformed plants that are derived from any of the transformation techniques described above may be grown for regenerating a whole plant that has the transformed genotype and then the desired phenotype as the essence or reduction of the formation of chitin structures of coleoperous insects such as the cuticle and/or the peritropohic membrane. Such regeneration techniques rely on the handling of certain phytohormones in a medium of growth of tissue culture, typically containing a biocidal and/or herbicidal marker, which should be introduced together with the desired nucleotide sequence. Regeneration of plants from protoplast culture is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985 (as mentioned in patent application US20020152501). The regeneration can be obtained through plant calli, explants, organs, or a part thereof. Such regeneration techniques are generally described in Klee et al., Ann. Ver. Of Plant Phys. 38:467-486, 1987 1985 (as mentioned in patent application US20020152501).

Without restricting the invention to a particular mode of action, it is expected that the enzyme in eukaryotic cells responsible for generating small RNA molecules with about 21 dsRNA nucleotide (as DICER in *Drosophila*) can be saturated by including an excess of dsRNA sequences (that is, complementary RNA molecules) which are not related to the nucleotide sequence of the target gene or of the gene to be silenced.

The natural variation in the post-transcriptional regulation of the expression of the target gene occurring between different lines of eukaryotic organisms comprising the same dsRNA molecule will be replaced by handling the gens silencing spectrum. This fact may take place by including the nucleotide sequences of extra dsRNA not related to the target gene, which are operatively linked to the dsRNA formed by the first and second regions.

The embodiments of the present invention can be effective against a number of pests. For the purposes of the present invention, the pests include, but are not limited to insects, fungi, bacteria, nematodes, acarids, protozoan pathogen, animal parasites, and the like. Pests of particular interest are insect pests, particularly insect pests that cause significant damages to agricultural plants. By "insect pests" one understands insects and other similar pests such as the insects of the orders: Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularmente Coleoptera, especialmente *Anthonomus grandis, Diabrotica virgifera, Tenebrio molitor, Tribolium castaneum*, Phoracantha *semipunctata, Lixus angustatus, Acanthoscelides obtectus* and other coleoptera that cause damages to woods and agronomically important plants of the families: Scolytidae, Cerambycidae, Curculionidae and Bostrichida. Insect pests of the present invention of most cultivars include, but are not limited to: Corn—*Ostrinia nubilalis, Agrotis ipsilon, Helicoverpa zea, Spodoptera frugiperda, Diatraea grandiosella, Elasmopalpus lignosellus, Diatraea saccharalis, Diabrotica virgifera virgifera, Diabrotica* longicomis *barberi, Diabrotica* undecimpunctata howardi, Melanotus spp., Cyclocephala *borealis, Cyclocephala immaculata, Popillia japonica, Chaetocnema pulicaria, Sphenophorus maidis, Rhopalosiphum maidis, Anuraphis maidiradicis, Blissus leucopterus leucopterus, Melanoplus femurrubrum, Melanoplus sanguinipes, Hylemya platura*, Agromyza parvicornis, Anaphothrips obscrurus, *Solenopsis* milesta, *Tetranychus urticae*; Sorgo—*Chilo* partellus, *Spodoptera frugiperda, Helicoverpa zea, Elasmopalpus lignosellus, Feltia subterranea, Phyllophaga crinita*, Eleodes, Conoderus, e Aeolus spp., *Oulema melanopus, Chaetocnema pulicaria, Sphenophorus maidis, Rhopalosiphum maidis, Sipha flava, Blissus leucopterus leucopterus, Contarinia sorghicola, Tetranychus cinnabarinus, Tetranychus urticae*; Wheat—Pseudaletia unipunctata, *Spodoptera frugiperda, Elasmopalpus lignosellus, Agrotis orthogonia, Elasmopalpus lignosellus, Oulema melanopus, Hypera punctata, Diabrotica* undecimpunctata howardi, *Schizaphis graminum, Macrosiphum avenae, Melanoplus femurrubrum, Melanoplus differentialis, Melanoplus sanguinipes, Mayetiola destructor*, Sitodiplosis mosellana, Meromyza americana, Hylemya *coarctata, Frankliniella fusca*, Cephus cinctus, Aceria *tulipae*; Sunflower—Cylindrocupturus adspersus, Smicronyx fulus, Smicronyx *sordidus*, Suleima helianthana, Homoeosoma electellum, Zygogramma exclamationis, Bothyrus gibbosus, Neolasioptera murtfeldtiana; Cotton—*Heliothis virescens*, lagarta-das-maçãs; *Helicoverpa zea*, ear-of-corn caterpillar; *Spodoptera exigua, Spodoptera frugiperda* caterpiller; *Pectinophora gossypiella*, pink ballworm; *Anthonomus grandis*, boll-weevil; *Aphis gossypii*, cotton-plant louse; *Pseudatomoscelis seriatus*, cotton leaping flea; *Trialeurodes* abutilonea, white fly *Bemisia tabaci; Melanoplus femurrubrum*, gafanhoto; *Melanoplus differentialis*, grasshopper; *Thrips tabaci*, tripes-do-fumo; Franklinkiella *fusca*, tripes; *Tetranychus cinnabarinus*, ácaro vermelho; *Tetranychus urticae*, striped acarid; Rice—*Diatraea* saccharalis, *Spodoptera frugiperda, Helicoverpa zea, Colaspis brunnea, Lissorhoptrus oryzophilus, Sitophilus oryzae, Nephotettix nigropictus, Blissus leucopterus leucopterus, Acrosternum hilare*; Soybean—*Pseudoplusia includens, Anticarsia gemmatalis, Plathypena scabra, Ostrinia nubilalis, Agrotis ipsilon, Spodoptera exigua, Heliothis virescens, Helicoverpa zea, Epilachna varivestis, Myzus persicae, Empoasca fabae, Acrosternum hilare, Melanoplus femurrubrum, Melanoplus differentialis, Hylemya platura, Sericothrips variabilis, Thrips tabaci, Tetranychus turkestani, Tetranychus urticae*; Barley—*Ostrinia nubilalis, Agrotis ipsilon, Schizaphis graminum, Blissus leucopterus leucopterus; Acrosternum hilare, Euschistus servus, Jylemya platura, Mayetiola destructor, Petrobia latens*; Canola—Vrevicoryne *brassicae, Phyllotreta cruciferae, Phyllotreta striolata, Phyllotreta nemorum, Meligethes aeneus, Meligethes rufimanus, Meligethes nigrescens, Meligethes canadianus*, and *Meligethes* viridescens; Potato—*Leptinotarsa decemlineata.*

EXAMPLES

The present invention is further defined in the following Examples. One should understand that these Examples, while indicating a part of the invention, are given illustratively only, without being limitative of the scope of the present inventions.

Usual techniques of molecular biology such as transformation of bacteria and gel electrophoresis of agarose of nucleic acids are referred to by common terms to describe them. Details of the practice of these techniques, well known from the prior art, are described Sambrook, et al. (Molecular Cloning, A Laboratory Manual, 2nd ed. (1989), Cold Spring Harbor Laboratory Press). Various solutions used in experimental handling are referred-to by their common names such as "lysis solution", "SSC", "SDS", etc. The compositions of these solutions can be found in reference Sambrook, et al. (supracitada).

Example 1—Identification of Nucleotide Sequence of the Enzymes Chitin Synthase 1 and Chitin Synthase 2 of *Anthonomus grandis* for Preparing the dsRNA Eggs, larvae and adult insects of *A. grandis* were obtained from the Laboratório de bioecologia e semioquímicos de insetos da Embrapa Recursos Genéticos e Biotecnologia em Brasília-DF. The colony was fed with artificial diet as described by Monnerat et al (MONNERAT, R. G., et al., Criação massal do bicudo do algodoeiro *Anthonomus grandis* em laboratório. Comunicado Técnico, 46, Embrapa-Cenargen: Brasília, 2000), and kept at 26±2° C., relative humidity of 60±10% and photophase of 12 hours.

For cloning and sequencing of chitin synthase 1 and chitin synthase 2 of *A. grandis* the total RNA was isolated from eggs, larvae and adult insects by using Trizol (Invitrogen), the protocol indicated by the manufacturer. The cDNA was synthesized from 5 g de RNA total using the kit Superscript II™ First-Strand Synthesis System for RT-PCR (Invitrogen) using oligo NV-d(T)30-AP (Tabela I). For initial amplification of segments of chitin synthase 1 and chitin synthase 2 of *A. grandis*, one used degenerated primers corresponding to conserved regions found in catalytic domains of chitins synthases of other insects. One carried out two consecutive stapes of PCR using degenerated primers. The first PCR step consisted of amplifying the segment in the catalytic domain between the preserved amino acids DPDYYEFE (SEQ ID NO: 7) and LHPQE (SEQ ID NO: 8), using degenerated oligonucleotides for the sense primer oligonucleotide and for the antisense primer. The PCR conditions in this first step were as follows: 1 L diluted cDNA (1:20), 2.0 L buffer 10× High Fidelity, 0.8 L $MgSO_4$ (50 mM), 0.4 L dNTP (10 mM), 0.4 L of each oligonucleotide (10 M), 0.2 L (1 U) Taq Platinum® High Fidelity (Invitrogen) and 14.8 L $H_2O$. In the second step, one used as a mold the product of the first step 1:20 and used primer oligonucleotides between the DGDIDF (SEQ ID NO: 9) regions (sense primer) and QYDQGEDRW (SEQ ID NO: 10) or GPGTIFLM (SEQ ID NO: 11) (antisense primer). In the two steps the PCR reactions with the degenerated primers were carried out using the following conditions: 94° C. for 3 minutes, followed by 30 cycles of 94° C. for 30 seconds, 48° C. for 30 seconds and extension at 72° C. for 1 minute.

Figure 2:
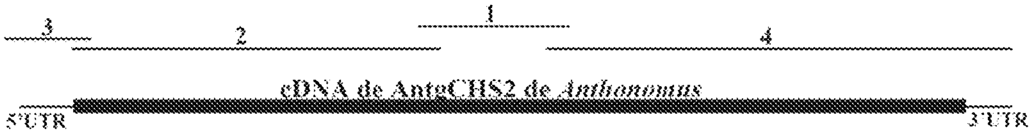
FIG. 2—Strategy of cloning the cDNA of AntgCHS2. The complete sequence of the cDNA of AntgCHS2 was determined by overlapping 4 fragments of PCR products.

In order to obtain the complete cDNA sequence of chitin synthases, the ends 5' and 3' were amplified using specific oligonucleotides designed from the preserved region sequenced previously. FIG. 1 illustrates the steps of cloning the cDNA of AntgCHS1 synthesized from the do RNA extracted from eggs of *A. grandis*. The oligonucleotides used in the cloning steps of AntgCHS1 are listed in Table I. On the other hand, FIG. 2 illustrates the steps of cloning the cDNA of AntgCHS2 synthesized from the RNA synthesized from larvae and adults of *A. grandis*. The oligonucleotides used in the steps of cloning AntgCHS2 are listed in Table II. The complete sequence of the cDNA of AntgCHS1 SEQ ID No 1 and of the cDNA of AntgCHS2 SEQ ID No 3 was obtained by overlapping the fragments obtained by the 5' and 3' RACE.

TABLE I

List of oligonucleotides used in cloning AntgCHS1

| Name of the oligonucleotide | No of the fragment (FIG. 1) | Size (pb) | Oligonucleotide Direction | Type | Sequence (5'-3') |
|---|---|---|---|---|---|
| NV-d(T)30-AP | | | A | D | GAATTCACGCGTCGACTAG TAGCATATGTAC(T)$_{30}$VN (SEQ ID NO: 12) |
| QuiSyntFor2010-DPD | | 1268 | S | D | GAYCCNGAYTAYTAYGART TYGAR (SEQ ID NO: 13) |
| QuiSyntRev3270-LHP | | | A | D | YTCYTGNGGRTGNA (SEQ ID NO: 14) |
| QuiSyntFor2400-DGD | 1 | 588 | S | D | GAYGGNGAYATYGAYTTY (SEQ ID NO: 15) |
| QuiSyntRev2960-GPG | | | A | D | CATVAGGAADATVGTDCCG GGDCCMAR (SEQ ID NO: 16) |
| 5'CHS1fw | 2 | 2530 | S | E | TTAATCGTTGTGGATATTT AATAG (SEQ ID NO: 17) |
| AntgCHS1cons ervadorv | | | A | E | GAAAAACATCCGGGACTAC ACAGTACGCA (SEQ ID NO: 18) |
| AntgCHS1cons ervadofw | | 2675 | S | E | CGGGGATATTGATTTCCAA CC (SEQ ID NO: 19) |
| AgQS1GTWc12 219rv | 3 | | A | E | TGACTTACACCAACTTATC C (SEQ ID NO: 20) |

TABLE II

List of oligonucleotides used in cloning AntgCHS2

| Name of the oligonucleotide | No of the fragment (FIG. 1) | Size (pb) | Oligonucleotide Direction | Type | Sequence (5'-3') |
|---|---|---|---|---|---|
| NV-d(T)30-AP | | | A | D | GAATTCACGCGTCGACTAG TAGCATATGTAC(T)30VN (SEQ ID NO: 12) |

TABLE II-continued

List of oligonucleotides used in cloning AntgCHS2

| Name of the oligonucleotide | No of the fragment (FIG. 1) | Size (pb) | Oligonucleotide Direction | Type | Sequence (5'-3') |
|---|---|---|---|---|---|
| QuiSyntFor2010-DPD | | | S | D | GAYCCNGAYTAYTAYGART TYGAR (SEQ ID NO: 13) |
| QuiSyntRev3270-LHP | 1268 | | A | D | YTCYTGNGGRTGNA (SEQ ID NO: 14) |
| QuiSyntFor2400-DGD | | | S | D | GAYGGNGAYATYGAYTTY (SEQ ID NO: 15) |
| QuiSyntRev2700-QYD | 1 | 324 | A | D | CCANCKRTCYTCNCCYTGR TCRTAYTG (SEQ ID NO: 21) |
| 5'-1AntgCHS2fw | 2 | 2601 | S | E | CAAATTTCTCAAAAATCGC CACC (SEQ ID NO: 22) |
| AntgCHS2conserv adorv | | | A | E | AACATGAGAAATATCGTTC C (SEQ ID NO: 23) |
| 5'-2AntgCHS2fw | | 731 | S | E | GGGATTTTGAAATCATACT TGGTA (SEQ ID NO: 24) |
| AntgCHS2-c8194-Rv | 3 | | A | E | GCGAGCATCAAAAACCATA TCC (SEQ ID NO: 25) |
| AgQSconservadofw | 4 | 2450 | S | E | CGGGGATATTGATTTCCAA CC (SEQ ID NO: 19) |
| GTW-AP | | | A | E | TCCGAATTCACGCGTCGAC TAGTAGCA (SEQ ID NO: 26) |

The design of the double-stranded RNA segment consisted in choosing fragments between 180 pb and 600 pb, (SEQ ID No 2, SEQ ID No 4, SEQ ID No 5 and SEQ ID No 6) by using, as a mold, the sequences of the cDNA AntgCHS1 and AntgCHS2. For the design of double-stranded RNA one used the program BLOCK-iT™ RNAi Designer (available at rnaidesigner.invitrogen.com/rnaiexpress), which analyzes the sequences and indicates regions of greater probability for use in gene silencing.

The DNA molds for the synthesis of the double-stranded DNA (dsRNA), by in vitro transcription were synthesized by PCR, the oligonucleotide sequences are listed in Table III. The selected target regions of the cDNA were amplified through PCR reactions using specific primers flanked by the minimum sequence of the promoter T7 (5'-TAATACGACT-CACTATAGGGAGA (SEQ ID NO: 27)) using the following conditions: 94° C. for 3 minutes, followed by 30 cycles of 94° C. for 30 seconds 60° C. for 30 seconds and extension at 72° C. for 1 minute. After amplification, the PCR products were cloned on the vector pGEM-T-easy for confirmation of the target sequence by sequencing. The PCR products of the target sequences obtained and sequenced without the regions of the sequence of the promoter T7 are described in the sequences SEQ ID No 2, SEQ ID No 4, SEQ ID No 5 and SEQ ID No 6. The detailing of the sequences SEQ ID No 4, SEQ ID No 5 and SEQ ID No 6 is described in Example 4.

TABLE III

Oligonucleotides used in the PCR reactions for synthesis of the molds for in vitro transcription of dsRNA

| Name of the oligonucleotide | Sequence of the oligonucleotide (5'-3') | Identification of the amplicom (pb) |
|---|---|---|
| AntgCHS1-dsRNAfw | TAATACGACTCACTATAGGGAGAATCACAGGAGCAGCGTTGC (SEQ ID NO: 28) | SEQ ID No 2 |
| AntgCHS1-dsRNArv | TAATACGACTCACTATAGGGAGAACACCAACTTATCCAATATC (SEQ ID NO: 29) | |

TABLE III-continued

Oligonucleotides used in the PCR reactions for synthesis of the molds for in vitro transcription of dsRNA

| Name of the oligonucleotide | Sequence of the oligonucleotide (5'-3') | Identification of the amplicom (pb) |
|---|---|---|
| AntgCHS2.1-dsRNAfw | TAATACGACTCACTATAGGGAGATCAAATTTCTCAAAATCG (SEQ ID NO: 30) | SEQ ID No 4 |
| AntgCHS2.1-dsRNArv | TAATACGACTCACTATAGGGAGAGCGAGCATCAAAAACCATATC (SEQ ID NO: 31) | |
| AntgCHS2.2-dsRNAfw | TAATACGACTCACTATAGGGAGACGGAGACATCGATTTCCAAC (SEQ ID NO: 32) | SEQ ID No 5 |
| AntgCHS2.2-dsRNArv | TAATACGACTCACTATAGGGAGAAACATGAGAAATATCGTTCC (SEQ ID NO: 33) | |
| AntgCHS2.3-dsRNAfw | TAATACGACTCACTATAGGGAGAAAGTAGACGCTCACGTATCC (SEQ ID NO: 34) | SEQ ID No 6 |
| AntgCHS2.3-dsRNArv | TAATACGACTCACTATAGGGAGATCTTCTGTGAATTGCTGCC (SEQ ID NO: 35) | |
| GusEC-dsRNAFw | TAATACGACTCACTATAGGGAGAGAACTGAACTGGCAGACTATC (SEQ ID NO: 36) | Negative |
| GusEC-dsRNARv | TAATACGACTCACTATAGGGAGAGCGGGTAGATATCACACTCTGT (SEQ ID NO: 37) | control |

After confirmation of the mold sequence, the synthesis of dsRNA was carried out using 0.5 μg of the PCR product of the sequences SEQ ID No 2, SEQ ID No 4, SEQ ID No 5 and SEQ ID No 6, flanked with the promoter region of the RNA polymerase of the T7, as a mold for a volume of transcription reaction of 20 μL, as described in the protocol of the manual of the kit MEGAscript® T7 High Yield (Ambion), the reaction contained 7.5 mM of each ribonucleotide ATP, CTP, GTP and UTP, buffer 1× and 50 U of T7 RNA polymerase.

The reaction was incubated for 16 hours at 37° C., followed by treatment with DNAse I for 15 minutes. For alignment of the double-stranded RNA, the reaction products were incubated at 70° for 5 minutes and cooled at room temperature (22° C.). For purification of the transcription products, one carried out extraction with phenol/chloroform and subsequent precipitation with isopropyl alcohol, as according to protocol described by the manufacturer of the kit MEGAscript® T7 High Yield (Ambion). The dsRNA was dissolved in water treated with DEPC. The integrity of the dsRNA was evaluated by gel electrophoresis of 1% agarose and the quantification was obtained by spectrophotomemetry. The final concentration of each dsRNA was adjusted to 200 ng/L to be used in the microinjection assays for evaluation of the gene silencing.

Example 2—Bioassays of Microinjection of dsRNA in *Anthonomus grandis*

Quantified samples of double-stranded RNA (dsRNA) were used in bioassays against the boll-weevil. The dsRNA was prepared from sequences identified as described in Example 1. For the procedure of microinjection in *A. grandis* adult insects and larvae were previously anesthetized in ice for 10 minutes. The microinjection was carried out by using a syringe Hamilton de 10 L, on each infects one applied 1 L of aqueous solution contain or not containing the dsRNA. The injection to the larva was carried out in the dorsal region between the fourth and the fifth abdominal segment. In the adult insects there was a need to raise one of the elytra to expose the abdomen, site of the microinjection. After the injection, the insects were: 1) kept in standard feeding conditions on artificial diet as described by Monnerat et al (MONNERAT, R. G., et al., Criação massal do bicudo do algodoeiro *Anthonomus grandis* em laboratório. Comunicado Técnico, 46, Embrapa-Cenargen: Brasília, 2000); 2) withdrawn when necessary according to the experimental period; 3) frozen in liquid nitrogen and stocked at −80° C. until the momento f extraction of the total RNA.

Example 3—Bioassays of Microinjection of dsRNA in *Anthonomus grandis* for Functional Analysis of AntgCHS1

The evaluation of the silencing of AntgCHS1 on phenotype parameters of females of *A. grandis* was determined by bioassays of microinjection of dsRNA AntgCHS1 (SEQ ID No 2) in adult females. The quantified phenotype parameters were oviposition, viability of eggs and mortality of the adult insect. Each experimental unit consisted of 16 adult females with 48 hours of age microinjected with 200 ng of dsRNA and 8 non-microinjected adult male insects the experimental period was of 12 days. The insects were kept in small cages, where the cage floor was made from fabric to enable collection of eggs. The male insects were marked with silvery glitter to facilitate identification. The monitoring of the bioassay was made every 48 hours, a moment when water and artificial diet were offered to ad libitum. The bioassay consisted of three biological replicas with three technical replicas. The control treatment consisted in applying dsRNA of a non-related gene, in this case one used dsRNA with sequence of the gene gus of *Escherichia coli*. In order to analyze the data obtained in the bioassays, one applied a variance analysis, followed by the Tukey multiple comparison test, at the level of 5% of significance. The eggs obtained from this experiment were subjected to analysis of the expression of AntgCHS1 by PCR in real time, as described in example 5.

In order to evaluate the silencing effect AntgCHS1 on the formation of newborn larvae, eggs obtained from the silencing experiment described before were perforated mechanically with entomologic nippers to break the egg shell and enable eclosion of the larvae. The larvae were kept on artificial diet for seven days. After this period, the larvae were counted and the phenotypes were analyzed. The eggs of the control treatment (dsRNA GUS) were also subjected to the same process of perforating their shell.

In order to analyze the biologic function of AntgCHS1 during the development of pupas of *A. grandis*, larvae of third instar were microinjected with 200 ng of dsRNA AntgCHS1. Each experimental unit consisted of 20 larvae. The bioassay consisted of three biologic replicas with three technical replicas. The experimental period was of 10 days. After this period, the larvae were counted and the phenotypes obtained were analyzed and photographed.

Example 4—Bioassays of Microinjection of dsRNA AntgCHS2 in *Anthonomus grandis* for Functional Analysis of AntgCHS2

In the microinjection assays with a view to the analysis of the silencing of enzyme chitin synthase 2 (AntgCHS2) one evaluated a number of variables as described hereinafter: 1—influence of the size of the segment of dsRNA; 2—location of the sequence of the target dsRNA within the sequence of the cDNA de AntgCHS2 (SEQ ID No 3); 3—effect of the concentration of dsRNA microinjected; 4—persistence of the silencing during the phases of development of the insect. The details of these experiments are described hereinafter.

1-Location of the Target Sequence within the Sequence of cDNA of AntgCHS2 and of the Size of the Segment of dsRNA for the Silencing:

In order to evaluate the effect of the position of the target sequence within the sequence of the cDNA of AntgCHS2 for the silencing, one selected three regions for synthesis of the dsRNA: the dsRNA localized at the end 5', called AntgCHS2-1 (SEQ ID No 4), comprising the region between the nucleotides 425-638 of the cDNA of AntgCHS2; the dsRNA localized in the central region, called AntgCHS2-2 (SEQ ID No 5), comprising the region between the nucleotides 2379-2966 of the cDNA; and the dsRNA localized at the end 3', called AntgCHS2-3 (SEQ ID No 6), comprising the region between the nucleotides 4373-4557 do cDNA. The segments chosen for the analysis of the dsRNAs had the sizes of 213, 587 and 184 pairs of bases, respectively.

In this assay one microinjected 200 ng of dsRNA per adult insect in a total of 12 insects. After 72 hours, four insects were selected at random, frozen in liquid nitrogen and kept at −80° C. The synthesis of the cDNAs of the different sizes, as well as the analysis by qRT-PCR, was carried out as described in example 5. One carried out two control treatments, one consisted in applying water treated with DEPC, and the other control consisted of microinjection of dsRNA GUS.

2—Effect of the Microinjected Dose of dsRNA

In order to evaluate the effect of the microinjected concentration of dsRNA on the silencing AntgCHS2, one tested the concentrations of 50, 100 and 200 ng of dsRNA AntCHSB-3/insect (SEQ ID No 6). This dsRNA was chosen from among the three available, since it is specific for *A. grandis*, and keep the size (184 pb), which reduced the possibility of the effect cross silencing with non-target genes. In this assay, a total of 12 adult insects were microinjected. After 72 hours, four insects were selected at random, frozen in liquid nitrogen and kept at −80° C. The synthesis of the cDNAs of different treatments, as well as the analysis by qRT-PCR, was carried out as described in example 5.

3—Persistence of the Silencing During the Phases of Development of the Insect.

Larvae were microinjected with dsRNA in order to evaluate the persistence of the effect of the RNAi on adult insect. Herein we adopt the nomenclature laRNAi (RNAi larval), suggested by Huvenne and Smagghe for this type of experiment (HUVENNE, H., et al., Mechanisms of dsRNA uptake in insects and potential of RNAi for pest control: A review. Journal of Insect Physiology, v. 56, n. 3. p. 227-235. 2010). The larvae of third instar of development were microinjected with 200 ng of dsRNA AntgCHS2-3 (SEQ ID No 6) and placed on artificial diet. Adult insects with age of 72 hours were subjected to the PCT analyses in real time, as described in example 5.

The evaluation of the silencing of AntgCHS2 on phenotypic parameters of females of *A. grandis* was carried out by means of microinjection bioassays on adult females. The quantified phenotypic parameters were oviposition, viability of eggs and mortality of the adult insect. Each experimental unit consisted of 16 adult female insects with 48 hours of age microinjected with 200 ng of dsRNA and 8 non-microinjected adult male insects the experimental period was of 12 days. The insects were kept in small cages, where the cage floor was made from web to facilitate identification. The monitoring of the bioassay was carried every 48 hours, a moment when water and artificial diet were offered ad libitum. The bioassay consisted of three biologic replicas with three technical replicas. The control treatment consisted in applying dsRNA of a non-related gene; in this case, one used dsRNA with sequence of gus gene of *E. coli*. In order to analyze the data obtained in the bioassays one applied a variance analysis, followed by the Tukey multiple comparison test, at the level of 5% of significance.

Example 5—Determination of the Levels of Expression of AntgCHS1 and AntgCHS2

For evaluation of the effect of the dsRNA on the expression of the target transcript (AntgCHS1 and AntgCHS2), one used the qRT-PCR technique (real-time quantitative PCR) (KUBISTA, M., et al., The real-time polymerase chain reaction. Molecular aspects of medicine, v. 27, n. 2-3. p. 95-125. 2006). The total RNA of insects from each treatment was isolated by using Trizol (Invitrogen), followed by the protocol indicated by the manufacturer. The cDNA was synthesized by using the kit SuperScript™ III Reverse Transcriptase (Invitrogen) from 1 g of total RNA treated with Ambion® DNAse I RNAse-Free™ (Invitrogen) using the oligonucleotide NV-d(T)30-AP (see Table I).

The real-time PCR reaction was carried out on the equipment 7300 Real-Time PCR System (Applied Biosystems) using SYBR™ Green, as intercalation fluorophore. The sequences of the oligonucleotides used for evaluation of the transcripts are described on Table IV. Each reaction was carried out in 2 L of a dilution 1:20 of cDNA, 0.2 M of each oligonucleotide in a total volume of 10 L. The program for qRT-PCR consisted of a starting step at 95° C. for 10 minutes, followed by 40 cycles of 95° C. for 20 seconds, 60° C. for 30 seconds and 72° C. for 30 seconds. For analysis of the amplifications at Ct (cycle of the threshold) and the amplification effectiveness of each oligonucleotide (ranging from 90% a 100%) were finished by the program Real-time PCR Miner (www.miner.ewindup.info/) (ZHAO, S., et al., Comprehensive algorithm for quantitative real-time polymerase chain reaction. Journal of Computational Biology, v. 12, n. 8. p. 1047-1064. 2005). The analysis of the relative expression, based on the Cts values and using multiple genes was carried out on the program qBasePlus version 2.0 by the method of Pfaffl (PFAFFL, M. W., A new mathematical model for relative quantification in real-time RT-PCR. Nucleic Acids Research, v. 29, n. 9. p. e45. 2001). All the qRT-PCR experiments were carried out on two biologic replicas and three technical repetitions. The genes GAPDH and beta-Actina were used as reference genes. The statistical analysis was carried out by the Tukey test, at the significance level of 0.05% for comparison with the treatments.

TABLE IV

Oligonucleotides used in the PCR reactions in real time for analysis of the expression of AntgCHS1 and AntgCHS2

| Name of the oligonucleotide | Sequence of the sense oligonucleotide (5'-3') | Sequence of the antisense oligonucleotide (5'-3') | Size of the amplicom (pb) | Efficiency (%) |
|---|---|---|---|---|
| AntgCHS1-RT | TGCTCCTGATAGATTTGATG (SEQ ID NO: 38) | ATCCGGGACTACACAGTACGCA (SEQ ID NO: 39) | 174 | 105 |
| AntgCHS2-RT | AAGGCATTAACGGTGACGAC (SEQ ID NO: 40) | TCCAAGTCGTTGATGACTGC (SEQ ID NO: 41) | 120 | 101 |
| GAPDH-RT | AGATCGTCGAGGGTCTGATG (SEQ ID NO: 42) | AAGGCGGGAATGACTTTACC (SEQ ID NO: 43) | 166 | 99 |
| B-Actin-RT | CCTTTAACACCCCTGCTATG (SEQ ID NO: 44) | TGAGGTAGTCGGTCAAGTCA (SEQ ID NO: 45) | 192 | 102 |

Example 6—Results of the Bioassays of Microinjection of dsRNA and Evaluation of the Gene Silencing for Enzyme Chitin Synthase 1 in A. *Grandis* (AntgCHS1)

One identified the cDNA sequence of the gene of Chitin synthase 1 in 1 (or A) of *A. grandis*, the size of which was of 4831 nucleotides (SEQ ID NO 1). Within this sequence, one selected a region of 249 pb (SEQ ID NO 2) to serve as a mold for the analysis of the dsRNA molecule, as described in example 1.

Figure 3:
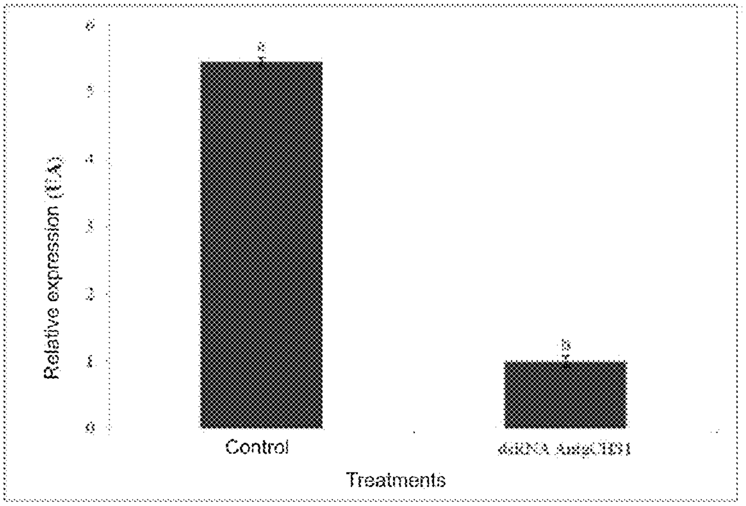
FIG. 3—Analysis of the relative expression of transcripts of AntgCHS1 in eggs of *A. grandis* by qPCR. actina and GAPDH were used as reference genes. The relative expression (UA) was calculated on the basis of the expression value for the treatment of dsRNA AntgCHS1, to which an arbitrary value of 1 was attributed. Different letters on the bars indicate a significant difference of the expression between the treatments based on two biological replicas ($P<0.05$, test-T). In the treatments of each insect was microinjected with 200 ng of dsRNA GUS (control) and 200 ng of dsRNA AntgCHS1.
Figure 4:
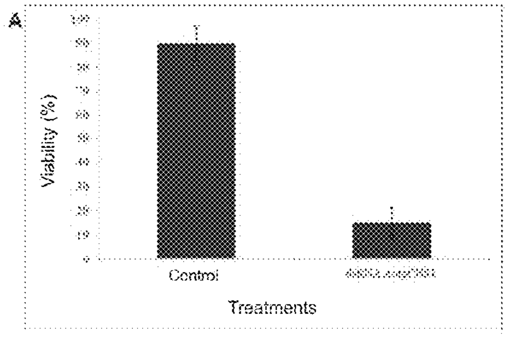
FIG. 4—Effect of the dsRNA of AntgCHS1 on the oviposition of eggs of *A. grandis*. A. Effect of the dsRNA of AntgCHS1 on the viability of eggs of *A. grandis*; B. Unviable eggs from females microinjected with dsRNA de AntgCHS1. In the treatments, each insect was microinjected with 200 ng of dsRNA GUS (control) and 200 ng of dsRNA AntgCHS1.
Figure 4:
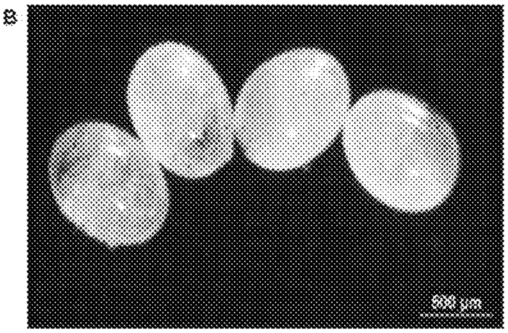
Figure 5:
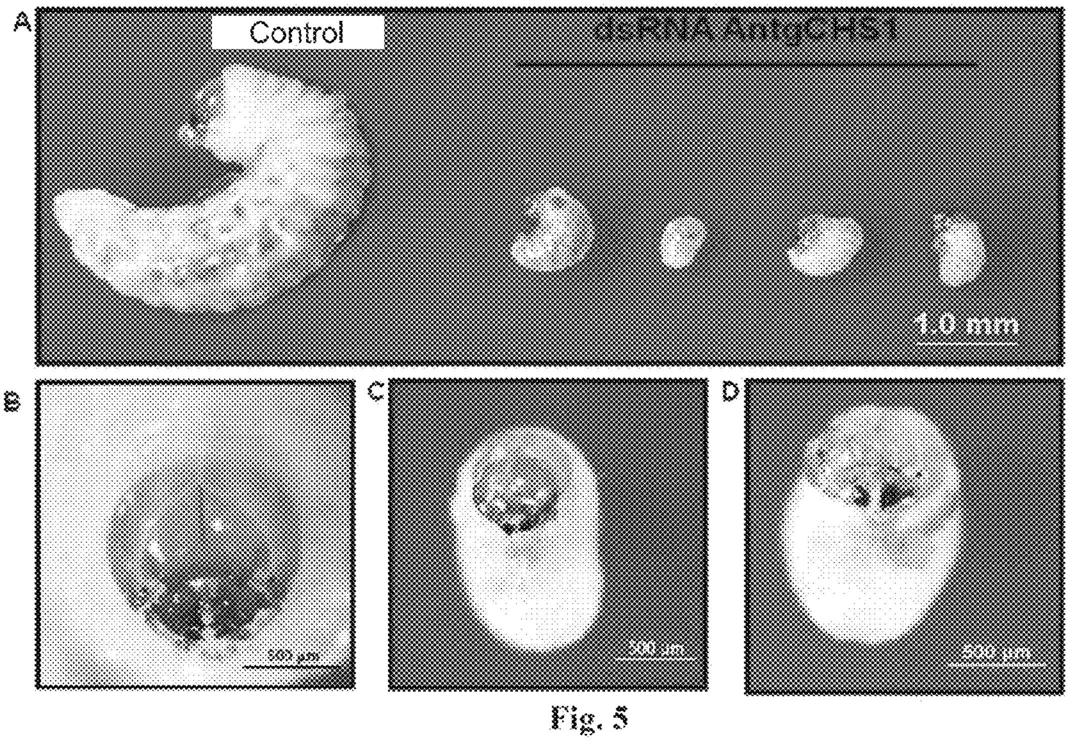
FIG. 5—Effect of the dsRNA of AntgCHS1 on the newborn larvae from adult microinjected insects of *A. grandis*. A. Larvae from adult microinjected with dsRNA of AntgCHS1; B detail of a control larva from adults microinjected with dsRNA GUS (control), C and D detail of larvae of first instar with malformations in the cephalic capsule.

One verified by means of the microinjection bioassays that the dsRNA AntgCHS1 (SEQ ID NO 2) was capable of suppressing the number of transcripts of Chitin synthase 1 in eggs of *A. grandis* (FIG. 3). In assays of microinjection of the dsRNA AntgCHS1 in adults of *A. grandis*, it caused reduction of the viability of the eggs (FIG. 4). It was observed that that the larvae formed within the eggs and moved actively, but did not eclose (FIG. 4). Some of these unviable eggs were perforated mechanically with the aid of nippers to for eclosion of the larvae. The perforated eggs were put on artificial diet for the development of the larvae. The larvae from the treatment with dsRNA AntgCHS1 exhibited malformations in the cephalic capsule and of the mandibles, and one observed the total mortality of the eclosed larvae from the treatment with dsRNA AntgCHS1 (FIG. 5).

Figure 6:
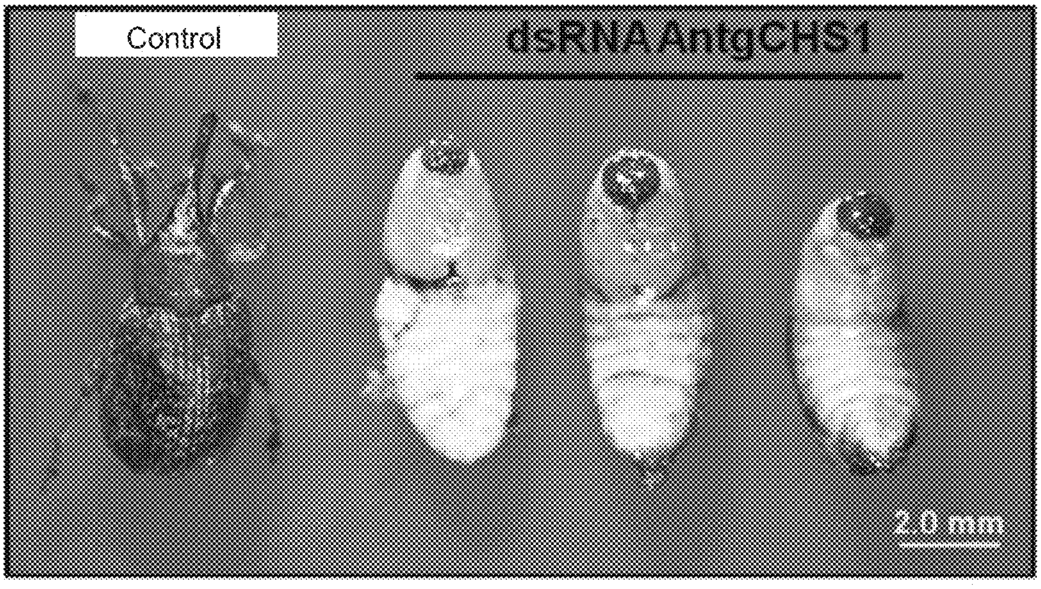
FIG. 6—Effect of dsRNA AntgCHS1 on the development of *A. grandis*. The microinjection of dsRNA AntgCHS1 was carried out on larvae of third instar. After microinjection the larvae were transferred to artificial diet to complete their development. After 10 days, the morphology of the insects was evaluated.

In experiments of microinjection of dsRNA AntgCHS1 (SEQ ID NO 2) in last instar larvae, it was observed that all the silenced insects either did not manage to develop in pupa or died. Non-silenced insects developed normally and became adults (FIG. 6).

Example 7—Results of the Bioassays of Microinjections of dsRNA and Functional Evaluation of the Gene Silencing for Enzyme Chitin Synthase 2 (AntgCHS2) in *A. grandis*

Figure 7:
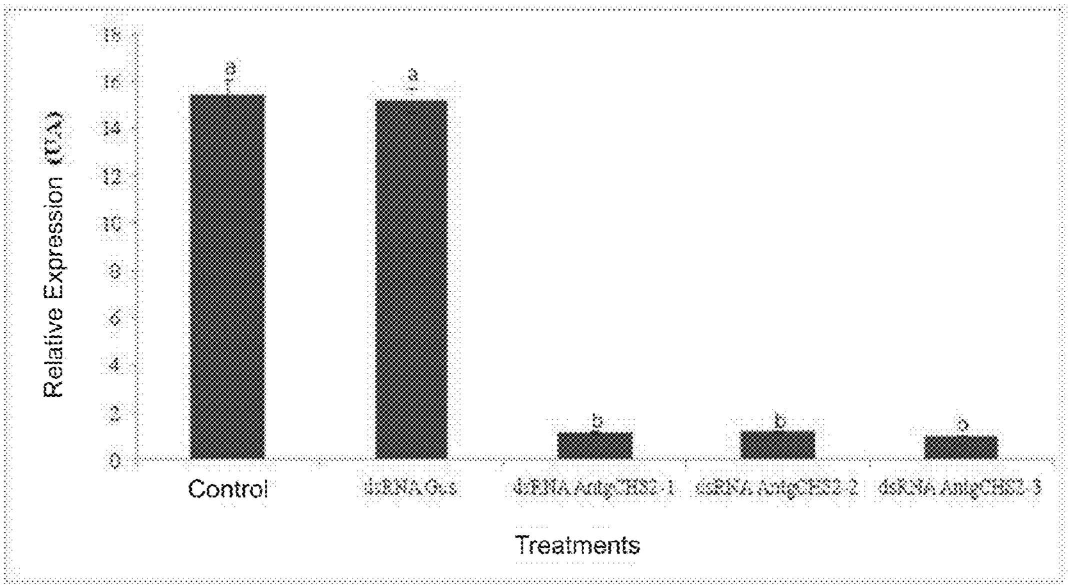
FIG. 7—Analysis of the relative expression of transcripts of AntgCHS2 after microinjection of different segments of dsRNA-genes of reference GAPDH and beta-actin 1. Control consisted in administering H2O; 2. dsRNA GUS—consisted in administering a dsRNA with the sequence of de 350 pb of the gene gus; 3. dsRNA AntgCHS2.1 (SEQ ID No 4); 4. dsRNA AntgCHS2.2 (SEQ ID No 5); 5. dsRNA AntgCHS2.3 (SEQ ID No 6).
Figure 8:
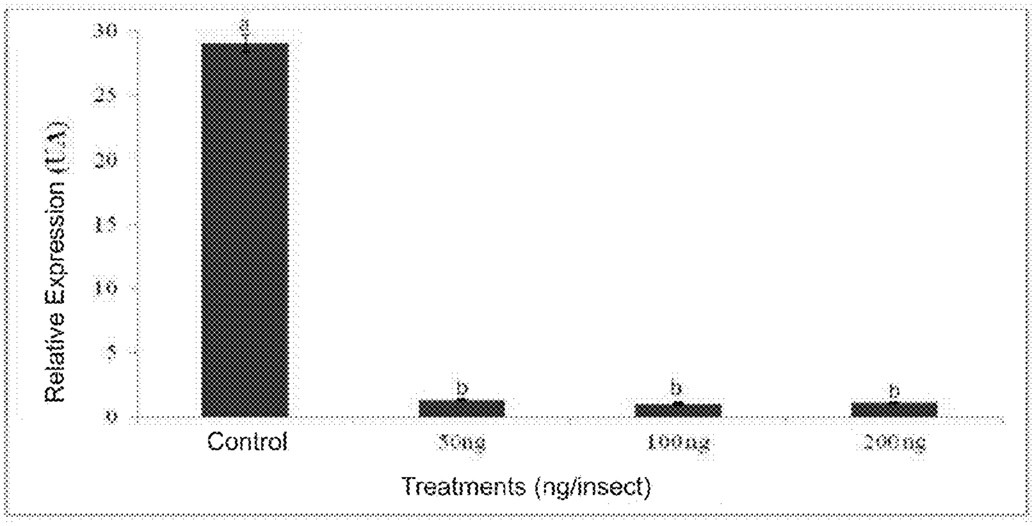
FIG. 8—Analysis of the relative expression of transcript by PCR in real time of AntgCHS2 after microinjection of different concentrations of dsRNA AntgCHS2.3 (SEQ ID No 6) in adult insects of *A. grandis* after 48 hs.
Figure 9:
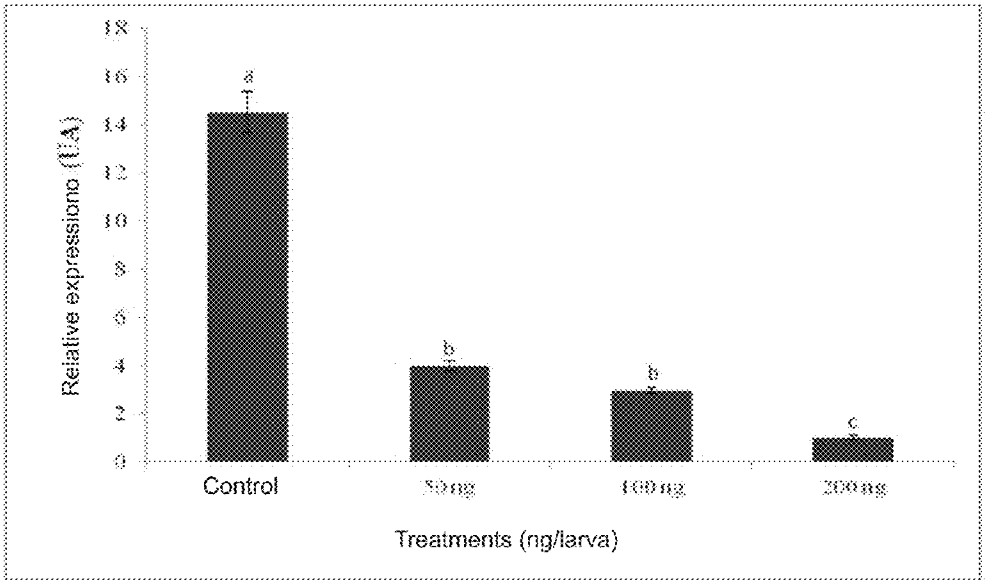
FIG. 9—Analysis of the relative expression of transcripts by PCR in real time of AntgCHS2 after microinjection of different concentrations of dsRNA AntgCHS2.3 (SEQ ID No 6) in larvae of *A. grandis* after 72 hs.
Figure 10:
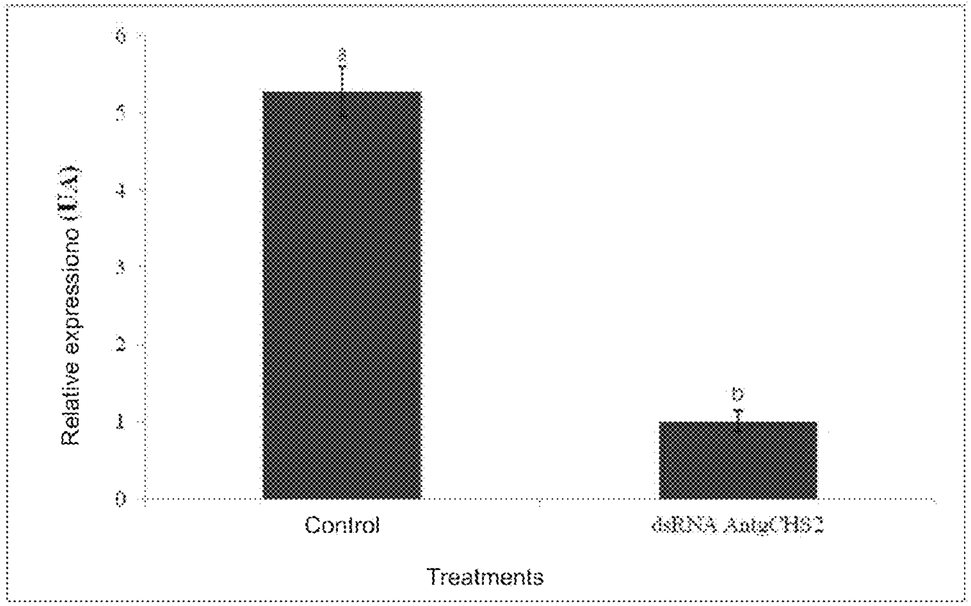
FIG. 10—Analysis of persistence of the silencing of AntgCHS2 after the larval development of *A. grandis* by PCR in real time. The microinjection of dsRNA AntgCHS2.3 (SEQ ID No 6) was carried out in larvae and the silencing was analyzed on adult insects of *A. grandis* após 72 hs from emergence.

On identified the sequence of cDNA of the gene of Chitin synthase 2 (or B) of *Anthonomus grandis*, the size of which was of 4729 nucleotides (SEQ ID NO 3). Within this sequence, one selected three regions of different sizes (SEQ ID NO 4, SEQ ID NO 5 and SEQ ID NO 6) to serve as mold for the synthesis of dsRNA molecules, as described in example. It was verified, by means of the microinjection bioassays and by the results of the real-time PCR analyses that dsRNAs of different sizes, ranging from 180 to 600 pb, were capable of suppressing the number of transcripts of AntgCHS2 without differing statistically between the treatments. In the same way, there was no difference between the regions chosen with target for the silencing, bit it at the end 5', in the central region, or still at the end 3' of cDNA (FIG. 7). Also, by real-time PCR analysis one observed that in adult insects microinjections of 50 ng of dsRNA were sufficient to cause a drastic reduction of the number of transcripts after 72 hours (FIG. 8). For the experiment of microinjection in larvae, the treatment that presented the greatest effect was the microinjection of 200 ng of dsRNA per insect (FIG. 9). It was verified that the effect of the gene silencing persists after the metamorphosis, that is, adults from microinjected larvae exhibited reduction of the number of transcripts of the chitin synthase 2 with respect to the control treatment (dsRNA GUS) (FIG. 10).

Figure 11:
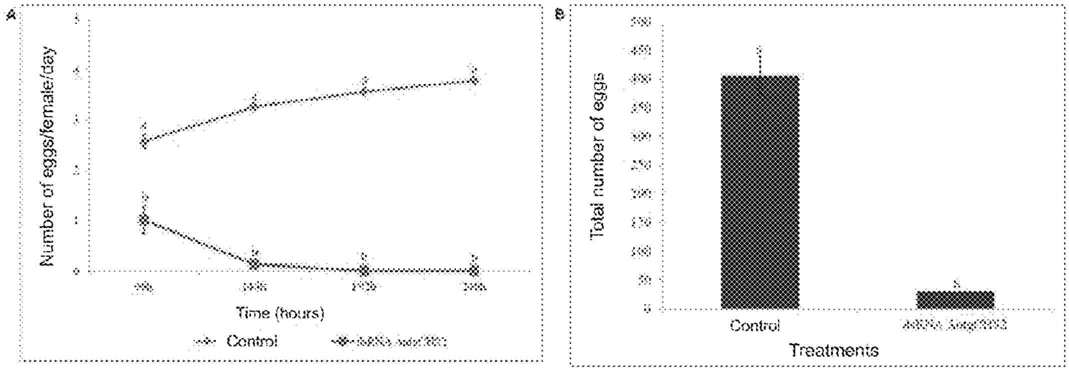
FIG. 11—Effect of microinjection of dsRNA AntgCHS2.3 (SEQ ID No 6) on the oviposition of females of *A. grandis*. In the control treatment, one administered dsRNA GUS; A—Analysis of the amount of eggs/female/day; B—Analysis of the oviposition of the number of total eggs. In the treatments, each insect was microinjected with 200 ng of dsRNA GUS (control) and 200 ng of dsRNA AntgCHS2.3.
Figure 12:
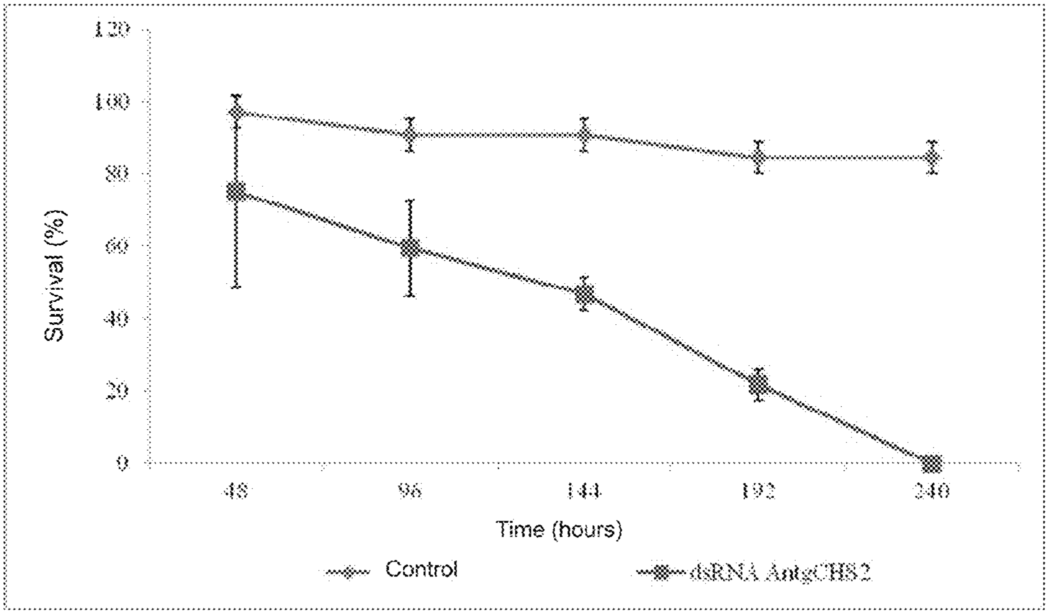
FIG. 12—Effect of the microinjection of dsRNA AntgCHS2.3 (SEQ ID No 6) on the survival of females of *A. grandis*. In the treatments, each insect was microinjected with 200 ng of dsRNA GUS (control) and 200 ng of dsRNA AntgCHS2.3.

In the evaluation of phenotypic parameters caused by microinjection of dsRNA AntgCHS2 (SEQ ID NO 6), it was found that, after 144 hours, the females microinjected with RNAi interrupted the oviposition, causing a reduction of 93% of the number of eggs (FIG. 11). Besides, the rate of mortality of the insects increased along the time, reaching 100% after 240 hours. On attributed to this lethal phenotype the initial interruption of the feeding that resulted in the interruption of the oviposition, followed by the death of the insect (FIG. 12).

The invention claimed is:

1. A chimeric gene, comprising:

a) a nucleic acid molecule comprising a nucleic acid sequence entirely complementary to a nucleotide sequence having at least about 95% sequence identity to a sequence selected from the group consisting of: SEQ ID NO: 3, SEQ ID NO: 4, SEQ ID NO: 5 and SEQ ID NO: 6; or b) a nucleic acid molecule comprising a first region and a second region which are transcribed into a ribonucleotide molecule, said first region comprising at least 23 contiguous nucleotides of a nucleic acid sequence selected from the group consisting of SEQ ID NO: 3, SEQ ID NO: 4, SEQ ID NO: 5 and SEQ ID NO: 6, and said second region comprising a nucleotide sequence entirely complementary to said first region; and c) a heterologous active promoter, operatively linked to the nucleic acid molecule of a) or b);

wherein ingestion by a coleopteran pest, of a ribonucleotide molecule transcribed from the nucleic acid molecule of a) or b), inhibits or reduces the proliferation of said pest.

2. A gene construct comprising one or more chimeric genes as defined in claim 1.

3. A gene construct according to claim 2, wherein said one or more chimeric genes comprise:

(a) a first region comprising a nucleic acid sequence of at least 23 contiguous nucleotides, having at least 23 contiguous nucleotides of a sequence of sense nucleotides selected from the group consisting of SEQ ID NO: 3, SEQ ID NO: 4, SEQ ID NO: 5 and SEQ ID NO: 6;

(b) a second region comprising a nucleotide sequence of about 23 contiguous nucleotides having at least 23 contiguous nucleotides of a sequence of sense nucleotides selected from the group consisting of SEQ ID NO: 3, SEQ ID NO: 4, SEQ ID NO: 5 and SEQ ID NO: 6.

4. The gene construct according to claim 3, wherein the first and the second region are capable of forming a double-stranded region, which may have, in addition to the total length of the first and of the second region, a spacing region between them containing at least about 3 nucleotides.

5. The gene construct according to claim 4, wherein the spacing sequence is an intron.

6. A vector characterized by comprising the chimeric gene according to claim 1.

7. The vector according to claim 6, wherein said vector promotes the expression of the molecule of interest or a fragment thereof.

8. A ribonucleotide molecule, characterized by being produced from the expression of the chimeric gene according to claim 1.

9. The ribonucleotide molecule according to claim 8, wherein said ribonucleotide molecule is a double-stranded ribonucleotide.

10. A transformed cell comprising the chimeric gene of claim 1.

11. The cell according to claim 10, wherein said cell is a prokaryotic cell.

12. The cell according to claim 10, wherein said cell is a eukaryotic cell.

13. The cell according to claim 10, wherein said cell is a plant or bacterial cell.

14. A transformed plant, characterized by comprising the chimeric gene of claim 1.

15. The plant according to claim 14, characterized in that the nucleic acid molecule is expressed in a plant cell, in the form of a double-stranded ribonucleotide sequence, and the ingestion of diet containing an inhibiting amount, to insect pest, of said double-stranded ribonucleotide sequence inhibits or reduces the proliferation of said pest.

16. The plant according to claim 15, wherein the insect pest is selected from the group consisting of *Anthonomus grandis, Diabrotica virgifera, Tenebrio molitor, Tribolium castaneum* and *Hypothenemus hampei, Phoracantha semipunctata, Lixus angustatus, Acanthoscelides obtectus* and other coleoptera that cause damages to woods and agronomically important plants of the families Scolytidae, Cerambycidae, Curculionidae and Bostrichida and other coleoptera.

17. A commercial product produced from a plant comprising the chimeric gene of claim 1, wherein said commercial product comprises a detectable amount of the chimeric gene of claim 1, or of a ribonucleotide expressed therefrom.

18. The ribonucleotide molecule according to claim 9, wherein the ingestion or assimilation, by coleopteran pest, of the double-stranded ribonucleotide, inhibits or reduces the proliferation of said pest.

19. A method for producing transgenic eukaryotic organisms, in which the expression of a target gene in the cells of the organism is reduced, said method comprising the steps of:

I) inserting the chimeric gene of claim 1 into a cell or cells of the organism to produce a transgenic cell or cells; and II) growing or regenerating a transgenic eukaryotic organism of the transgenic cell or cells.

20. A method for controlling infestation of coleopterans, said method comprising supplying, in the diet of a coleopteran pest an agent comprising the chimeric gene according to claim 1, or the ribonucleotide molecule of claim 9.

21. The method according to claim 19, wherein the eukaryotic organism cell further comprises a polynucleotide sequence encoding a pesticidal agent.

22. The method according to claim 21, wherein the pesticidal agent is selected from the group consisting of patatin, an insecticidal protein of *Bacillus thuringiensis*, an insecticidal *Xenorhabdus* protein, an insecticidal *Photorhabdus* protein, an insecticidal *Bacillus laterosporous* protein, an insecticidal *Bacillus sphaericus* protein, enzymes of the family of chitinase and a lignin.

23. The method according to claim 19, wherein the coleopteran pest is selected from the group consisting of *Anthonomus grandis, Diabrotica virgifera, Tenebrio molitor, Tribolium castaneum* e *Hypothenemus hampei, Phoracantha semipunctata, Lixus angustatus, Acanthoscelides obtectus* and other coleopterans that cause damages to woods and agronomically important plants of the families Scolytidae, Cerambycidae, Curculionidae and Bostrichida and other coleopterans.

24. The method according to claim 19, wherein the actuation mode of the nucleic acid molecule or of the double-stranded ribonucleotide sequence, upon being ingested or assimilated by the pest, is that of suppression or reduction of the expression of a gene that performs a function that is essential to the survival of the insect.

25. The method according to claim 24, wherein the function essential to the survival of the insect is selected from the group of differentiation and development of the cuticle, formation of the egg, larval maturation, transition of larval stage, pupation, digestion and assimilation of nutrients, protection against pathogens.

26. A method for improving the yield of cultivated plants subject to infestation by insect pests, said method comprising the steps of:

a. introducing the chimeric gene according to claim 1 into said plant;

b. growing the plant obtained in step a so as to enable expression of said nucleic acid molecule, wherein this expression inhibits or reduces proliferation of said pests.

27. The method according to claim 26, wherein the expression of the nucleic acid molecule produces an RNA molecule that suppresses at least one first target gene in an insect pest that has ingested a portion of said plant, wherein said target gene performs at least one function that is essential to survival of the insect to be selected from the group of differentiation and development of cuticle, egg formation, larval maturation, larval stage transition, pupation, digestion and assimilation of nutrients, and protection against pathogens.

28. The method according to claim 27, wherein the insect pest is selected from the group consisting of *Anthonomus grandis, Diabrotica virgifera, Tenebrio molitor, Tribolium castaneum* and *Hypothenemus hampei, Phoracantha semipunctata, Lixus angustatus, Acanthoscelides obtectus* and other coleopterans that cause damages to woods and agronomically important plants of the families Scolytidae, Cerambycidae, Curculionidae and Bostrichida and other coleopterans.

29. A method for producing a commercial product, comprising obtaining the transformed plant as defined in claim 14 and preparing a commercial product from the transformed plant.

30. A method of producing a food or animal feed, comprising obtaining the transformed plant as defined in claim 14 and preparing a food or animal feed from said transformed plant.

31. A method for controlling infestation of coleopterans, characterized in that it comprises supplying, in the diet of a coleopteran pest an agent comprising the ribonucleotide sequence according to claim 8.

* * * * *

SEQUENCE LISTING

<160> NUMBER OF SEQ ID NOS: 45

<210> SEQ ID NO 1
<211> LENGTH: 4831
<212> TYPE: DNA
<213> ORGANISM: Anthonomus grandis

<400> SEQUENCE: 1
ttaatcgttg tggatattta atagaattat tagaaatgac agcgaacata cgaaacgacg 60
cgagctatag cgacgacaat ttctctgacg acgaaagttc tccactcacg gaaaacatct 120
atggaggaag tagtaggaca gtccaggaaa caaaaggatg ggacgttttc cgaggaccct 180
ccgatcaagg aggagtccgg ttccaatggc aaaccaaaaa atgtctggaa attaccgtaa 240
aaatactaaa atacgtggca tatttggtaa cctttataat tgtacttgga tctggagtga 300
tatcgaaggg cacgttatta tttatgacct cacaacttag ggaaaataag atcgtaccct 360
attgcaatag ggacttaggt agagaaaaac aattcatagt gaaactccca acgcaagagc 420
gagtggcctg gatgtggtgc atctttttcg ccttctgtgt gccacagttg ggcgcactct 480
tccgttccac caggatgtgc tactttaaat cgtccaaacg acctcccttt tcccatttct 540
tgatgatagt gattccagag accgcccaca ccattggact cgccctaatg gcgttctaca 600
tcctgccaga tatcgatgtg gtaaaaggag ccatgttgac caactgttta tgctttgttc 660
caggagttct aggtctactt tcaagaaaca acaaggaatc gggacgtttt attaaagtaa 720
tcatggatct cattgcgata tcggcgcaag ctactggatt catcgtatgg ccaatcatag 780
agaatcgagc ggacctctgg atcatccccg tcactatctt tcttatttcc atgggctggt 840
gggagaacta tatccccaag aactcaccac tgccgtttat caagaaaatt gggaaaatga 900
gggaaagttt tgacaagacc agatacttca cttacatgtt cgtttccatt tggaagatgc 960
tgatcttctt cttgacgata ttggtcgtat tacttataag ggaaggggaa actgctttct 1020
ttttcacgga gttttctgaa agctttaatg ttcatcctat aactgttata gagataaaac 1080
cagtactagg cggcacagtt ctcccggaca tctccgagat tatcccaaca ggtgacgaca 1140
ccgtaatcca atcgaacgac tggagtccga tctacgtgat gctcatcaac atcatcgcct 1200
cgtacttggc ttacatcttc ggcaagttcg cctgcaaaat catgatccag ggattctcgt 1260
acgctttccc ggtgaacctc actattcccg tgaccgtgtc cctactaata gccgcctgtg 1320
gactcaggaa tggcgatcca tgctttttcc atgaaacgct accggattat ttgttcttcg 1380
ggattccgaa cgtcagtttc ttgaacgatt tcatttcgca tcagcacgcg tggatttggt 1440
tgttgtggtt gctgtcgcag acctgggtga ctttgcacat ctggacgccc aagtgtgaac 1500
gtctggcgag gaccgagaaa ctctttgtgg tcccgatgta tgatgggttg ttgattgatc 1560
agagcctggg gatgaataga cgtcgtgatg atgaagcaga cgtgaaaacc gaagacctgg 1620
atgagatcca gaaggaaaaa gctgatgagt actacgaaac catttcaaac cacacagatg 1680
gatcttcacc gaaagtaatt aagagctctg ataacatcac caggatctac gcctgtgcta 1740
ccatgtggca cgagaacaag gaagaaatga ttgagttctt aaaatcgatc ttgaggcttg 1800
atgaagatca atcggccagg agggtggccc agaagtatct cagagtagtt gatccagatt 1860
attacgaatt tgaaacgcat attttcttcg atgacgcatt tgaaattgcc gatcataacg 1920
acgacgatac tcaggtgaac cgattcgtga aactcctcat tgctaccatt gatgaggcgg 1980
cctccgatgt ccatcagact cacattaggg tcagaccacc taagaagata cccactcctt 2040
atggaggtcg attaatatgg caactaccag gaaaaacgaa aatgatcgcc cacttgaagg 2100

-continued

```
acaaaatgaa gatccgtcac aggaaacgtt ggtcacaagt gatgtacatg tattaccttc   2160
ttggacatag actgatggag ctaccaatat ctgtggatcg aaaagaaaca attgctgaaa   2220
acacttatct attaaccctg gatggggata ttgatttcca accttcagct gtactgctcc   2280
tgatagattt gatgaaaaag aacaagaatc ttggtgctgc ttgtggacgt attcatccag   2340
taggttctgg accaatggtg tggtaccaac tattcgaata cgctattggt cattggctcc   2400
aaaaggccac cgagcacgtt attggttgcg tactgtgtag tcccggatgt ttttcacttt   2460
ttagaggaaa agcccttatg gacgacaatg ttatgaagaa atatactaca tgttctgccg   2520
aagcaagaca ctacgtccag tacgatcaag gagaagatag atggctctgc actctactgc   2580
tccagcgagg ctaccgagta gaatattcag ctgcctctga tgcctacact cacgccccag   2640
aaggtttcaa tgagttttac aatcagagac gtagatgggt tccctcgact atcgccaaca   2700
tcatggactt gctaatggac tctaaaagga ccatagaagt aaacgacaac atttctatgc   2760
cctacatagg ctaccagatc ttacttatgg gcggtaccat cttgggacct ggaactatat   2820
ttcttatgtt ggtgggtgcc ttcgtggccg cctttcaaat cgacaactgg accagctttt   2880
actataattt gtaccccatt atgttcttca tgcttgtgtg ttttacttgc aaatccaata   2940
tccagctgat agtggctcag atcctctcca cttgctatgc acttataatg atggccgtga   3000
tcgtgggtac tgcccttcag ttaagggagg acggcgtggg ttctccctct gccattttcc   3060
taattgccat gaccggatct ttctttatag cggcctgttt gcacccccaa gagttctggt   3120
gtattgtgcc agggatgatt tacctactct caataccttc tatgtacctg ctgctgatcc   3180
tgtattcgat tattaacttg aataacgtct cttgggggac gcgagaagta gctgtgaaaa   3240
aaaccaaaaa ggaactagaa gaagagaaga aacaagcaga agcagcaaag aaaaaagtca   3300
aaaacaaatc cctactaggt ttcctacaaa gcggaggaac aagtgacgac gacgagggca   3360
gtatcgagat ttcattggct ggactattca aatgtatgct ccgcacccac cagaaggccg   3420
gagatgaaaa agcccaattg attcatatcg gggaatcact ggatacactg caaaagagac   3480
tggatcacat tgaaaaagtg gtagatcctt ctggacatgc ctcaagaaaa cgcagcatgt   3540
cagcctcctc acgccacggt ggccacggtt ccgatcttca tcacttgagt gcagtcaatg   3600
aagatgctaa cgaagatgct tcttctgaat cagactcaga aagcaccagt acagtgcctc   3660
agaataagag agatgagttg gtgaatccct actggataga agatccggac gtcggcaagg   3720
gagaggtaga ataccttagc agcaccgaaa tacaattctg gaaggatctg ttggcgaaat   3780
atctgtatcc tttagatgaa aataaggagg aaaaggccag gatagcgtca gacttaaaag   3840
aactgaggga ccaatcggtg ttcgcctttt tcatgctgaa cgccttattc gtactaatcg   3900
tgttcttact gaccctgaaa aaggactatc tgcacatcaa atggccgttt ggagtaaaag   3960
cgaacattac ttacgatggt caagagctgg taatcaccaa ggaatacctc caactggaac   4020
ccatcggtct ggtattcgta ttcttcttcg ccttaattct ggtcatccag ttcgtcgcta   4080
tgttgttcca tagattcgga actattgccc atattttggc ctcaactgat ctcaacctat   4140
gcagcaaaaa gaaagaggaa atgtctccta acgccttatt ggacaagcaa gcggtcgaga   4200
tggtaaaaca attgcaaaaa ctccaaggaa ttgacgatgg ggattacgat aacgattcag   4260
gatcgggtcc ggaccgtatt gggcgcagaa aaaccattca taacatccag agggcggctc   4320
agaagaagtg gcaaattggt accctggatg tagcttttaa gaagagattc gccaaactta   4380
atgccaatcc aaatggcggt accccagtac tatccaggcg tatgaccatg ggcagagaaa   4440
```

-continued

```
ccatgaaagc tctcgaggtg cgcgtcaatt ccgttatggc ggaacgaaga aagtcccaca   4500

tgcaaaccct gggagcgaaa aacgattttt ccaataatac tgtgaccaat aacaacgtga   4560

ataatttaac aagaaatcac aggagcagcg ttgcaagtcc tattgctgct aaggatattt   4620

ttgaaaatgg gcatgtaaat aaggcgtatg aggaggagag cacttatggc agcaggaact   4680

ctttggcaat ggcgcaaaga gggcaacaat ggaaagggag taatagtaga atgtaaatag   4740

aaaattaaat aagtgagggt ttattgataa gtgaacgtat tttgcttgag gatcaagtta   4800

cgatgatatt ggataagttg gtgtaagtca g                                  4831
```

<210> SEQ ID NO 2
<211> LENGTH: 249
<212> TYPE: DNA
<213> ORGANISM: Anthonomus grandis

<400> SEQUENCE: 2

```
atcacaggag cagcgttgca agtcctattg ctgctaagga tatttttgaa aatgggcatg     60

taaataaggc gtatgaggag gagagcactt atggcagcag gaactctttg gcaatggcgc    120

aaagagggca acaatggaaa gggagtaata gtagaatgta aatagaaaat taaataagtg    180

agggtttatt gataagtgaa cgtattttgc ttgaggatca agttacgatg atattggata    240

agttggtgt                                                            249
```

<210> SEQ ID NO 3
<211> LENGTH: 4729
<212> TYPE: DNA
<213> ORGANISM: Anthonomus grandis

<400> SEQUENCE: 3

```
gggattttga aatcatactt ggtaatggat attttgttag tatcaaataa aaattaatct     60

tatcgggaaa cacgtcactt cgaatgtcgt cggttgatcg tgtctttctc agttctatga    120

taatatgttt atttttattt taactaacgc acggtaaatc ggacctacga aactgaaaag    180

tgcagtcagt taagtgtttt gtgacccaat ttgtgttcta ccgcacaaat ggacgaggat    240

tttgacgact ttgacgattt tgacgacgag gattctttgt taggatcaac agagaggcag    300

ggcgaagaag tgaaaccatg gaacaccttc aaggtgatcc acaggaaaac ggccagcgga    360

tccacagtcg aaaacaaact ggtggacaat ggagtcaaat ttctcaaaat cgccaccatt    420

tttatcacat ttttggtggt actaggtacg gcagtactat ccaagggatt gattctctta    480

atgacctcac agatcaagaa gaacgtcact aggaattatt gcaataaagg actagatatt    540

tcaaggcagt acatcttctc agttcccgga gttgaaagag ccacctggat atggtttttg    600

atgctcgcct actttgttcc tgaatttatg acattcttca ggtcaggacg aattctacta    660

ttcaaaacga gactctatcc aacccttacg gagtttctca gcctattagt aacagaatgt    720

ttaccagcaa taggcagcag tctgctaatt ttctgcgttc taccggaact cgatgtggtc    780

aaaggagcca tgctcactaa cgcaatgtgt gtgattccag cattaatgtt ggtttttacg    840

aaaattggta cgaaaaagat ctcaatagtc actgaaattg cggatatttt agcattgcta    900

gcgcagctat cagcgatgct cgcttggcca ctaataaatc acgacgaacc tatactgtgg    960

cttataccaa tttgtgccat tttaatctcg tttggttggt gggagaactt tgttccgtta   1020

tcatcaccaa taaaattggt acgacaattg gccaaatcca gaaaagagtt tcccacccgc   1080

aagtactttt gctactttat tatttcatcg gttaaatgta taattttctt cgcgaccact   1140

atagcttgca tatattttaa agatggcgat gtgaactttt tattcgagaa cttttccgat   1200
```

```
attttctgga atcatccgat gaccgttacc gaggttgttc cacaagtgac aggtaccaac   1260
atcaccgtag atgacgcaat cagcactggg atagtccaca taatctacag cgatatcaat   1320
cttcaggcag ccatttgggg cgtcagcgtc gtttccgctt atgcttgcta cgcctttggc   1380
aagtttgctt gcaaaattat gatccagggt tcaagttttg cttttccgat cgctttaact   1440
gtgcctttcc tcatatcagc tctggtgatc ttttgtggat tctatgccaa agacgtgtgt   1500
gccttctatg acttcttacc ggcatatctc ttctttaact caccaccctt gcttaacctc   1560
ttgaacttcg tggagactca acatccgtat ttatggctgt tttggctgct ttcccaaata   1620
tggatcacca ggcatatttg gaccaacaat aactcgaagc tggcttccac tgaaaagttg   1680
ttcatgcgtc ccatgtacga cgggatcctg atcgatcaat ccattgcaat gaatcgcaga   1740
aatgtcgtgg ataaacttgt agaggaggag aaactggcag acggattgga aagcaagaat   1800
atcattgacg agaataaaat aacaagaatc tacgcttgcg ctaccatgtg gcacgagact   1860
ccggaggaaa tgatggagtt cttcaagtct attttcagga tggacgagga ccaagcttgc   1920
taccggattt ctaggcagta cttacagtac cccggcgaag ggtattatga gtgggaaaca   1980
cacatctttt ttgatgatgc ctatttgaga aaatcagtaa acgacaacga tccaatgcta   2040
aactcctacg tgaacgattt tattgcaacc atgcccaaag ccgcagaaga agtgcataag   2100
acaacagtaa aaattcgacc tcctacaata tatcccactc cttacggggg cagactaata   2160
tgggtcctac caggaagaac aaaactcatc gtacatttaa aagacaaggc taagattagg   2220
gctaaaaaga gatggtctca agtgatgtac atgtattacc tgttaggaca caagttaatg   2280
gataatgaag aaatggatga taaaaaggtt aagctaagat catttaacac gtacatcctg   2340
gccctcgacg gagacatcga tttccaaccg gaagcagtcg ctttactagt ccagtatatg   2400
caaaaaaaga gcaacttagg agctgcttgt gggcgtattc atcctgtagg ttctggaatt   2460
atggcctggt atcaaacgtt cgaatacgca gtgggccatt ggatgcaaaa agcgaccgaa   2520
cacgtcatag gttgcgttct ttgttcgcca ggttgtttct ctctctttag agctagtgcc   2580
cttatggacc acaatgtaat ggctagatat acgacgcgtt cttccgaggc taggcattat   2640
gtacaatatg atcagggcga agatagatgg ctctgcaccc tcctactgca aaggggttac   2700
agagtggaat attctgctgc ctccgatgcc tatactcact gtccagaagg tttcatcgaa   2760
ttctacaatc aaagaaggag atggggaccg tctaccactg caaacatttt ggatctgctt   2820
gaggatagcg atcacatcaa gttggttaac gatgatatat cctctctata tatattttat   2880
caagtgattt taatgattgg cacagtgatt ggtcccggaa cgatatttct catgttggtc   2940
ggtgcgtttg ttacggtttt caatgtttcc cagtttacgg cgttgtggct caatgttggt   3000
cccattttgt ttttcgtgct cacttgtata atatgcaaat cggatacgca gttaatggtg   3060
gcagcaatac tgagcgcgat ctacggccta gtaatgataa tggtgctcat aggtgtcgcg   3120
atgcagatct acgacgatgg tgttctggcc ccttcttctc tgttcttctt cttaatgatg   3180
ggcgaatacg tggtagctgc aatgctccat ccaaaagagt tctactgtct taaatatggc   3240
gccatctact tgatcaccgt tccaagcatg tacatgttgc tcatcatcta ctctgtgttt   3300
aacatgaata acgtcagttg gggcaccagg gacgtcagcg tagcacctcc actgccagag   3360
ggccaaccga aacctccacc aaaaaaagaa aagtccttcg tagaagacgt actcgataaa   3420
atgaagaagt tctttatggc atgttgctcg ggagactcca agcatttagt tatgatcagt   3480
aattctttga cgcacattca atcaaaagtg gaacaaaata gacagaaagt cgaggatttg   3540
```

```
gagcggatca ctttggatcc agatgcggca gtgccaagga aaaccatggg aaaaaggaaa   3600

accactatta ttgaagggtc tagggcgtcg agacagtcac tccggaaatc aacgatgaac   3660

aaaccagggg ccatcccaaa tgaaaacgcc aatgcctcta ttgccgaaga tgatgaagaa   3720

gattatgatg aggaagagtc catcggtagc tcagacgatc ttcaaaacaa tagctggttc   3780

tacgcgggtg aactcctaag gggacgagtg actttcttgg ataaaaagga ggaaaagttt   3840

tggaaggagt tgctagatgc gtatttgcat cctattgaag atgataagga aaaagtggcc   3900

aaagacttga aagatctgag agacagaatg accatgagct tcttcgcact aaacgtattt   3960

tttgtcacgg tagtatttct tcttaccatt aagaaagaca tacttcactt aaattggccg   4020

ttcaatccca cggtgaactt cacttacagt gccgccagca gcatcaatga gattgtcgtt   4080

gaaaaaacct acttgcaact ggaacctata ggattcgtgt ttttgatctt cttcttcgcc   4140

ctcatggggt gcagttcttt gggatgttgc tccatcgatt tggcacgttt tccacaaatt   4200

atggccaaca ccgatgtcga gtttggagaa aagaagatag aaaacttgac cgaggacgaa   4260

ctactagaaa aagactctat aaaaatcgta aaaaaactgg tgaaactcaa aggcattaac   4320

ggtgacgacg agaaagacga ggaagtagac gctcacgtat ccagaaggaa aaccgtggcg   4380

gacttggcga aaaacaaaga cagaaaacgt gcagtcatca acgacttgga ttccgccttt   4440

taaagcccgt atggcaaaaa atacgtaaag gagaagacgc gtggagtggc tttacctagg   4500

aaaacttggc agcaattcac agaagaagaa caacagttct taagagaaaa tcaatgatgc   4560

cgcagttcaa tcccagcgcg tttaaggcgt ttaatcagca ttatggagag gagagtccta   4620

gcaggactat acatcatata gagaatcccg ggtatgatga tgatcctgct gacgcgtaga   4680

ttttatgtgc tagttgtttt agaattttta ataaataatt ttgggtctt              4729
```

<210> SEQ ID NO 4
<211> LENGTH: 214
<212> TYPE: DNA
<213> ORGANISM: Anthonomus grandis

<400> SEQUENCE: 4

```
tcaaatttct caaaatcgcc accattttta tcacattttt ggtggtacta ggtacggcag     60

tactatccaa gggattgatt ctcttaatga cctcacagat caagaagaac gtcactagga    120

attattgcaa taaaggacta gatatttcaa ggcagtacat cttctcagtt cccggagttg    180

aaagagccac ctggatatgg tttttgatgc tcgc                                214
```

<210> SEQ ID NO 5
<211> LENGTH: 588
<212> TYPE: DNA
<213> ORGANISM: Anthonomus grandis

<400> SEQUENCE: 5

```
cggagacatc gatttccaac cggaagcagt cgctttacta gtccagtata tgcaaaaaaa     60

gagcaactta ggagctgctt gtgggcgtat tcatcctgta ggttctggaa ttatggcctg    120

gtatcaaacg ttcgaatacg cagtgggcca ttggatgcaa aaagcgaccg aacacgtcat    180

aggttgcgtt ctttgttcgc caggttgttt ctctctcttt agagctagtg cccttatgga    240

ccacaatgta atggctagat atacgacgcg ttcttccgag gctaggcatt atgtacaata    300

tgatcagggc gaagatagat ggctctgcac cctcctactg caaaggggtt acagagtgga    360

atattctgct gcctccgatg cctatactca ctgtccagaa ggtttcatcg aattctacaa    420

tcaaagaagg agatggggac cgtctaccac tgcaaacatt ttggatctgc ttgaggatag    480
```

cgatcacatc aagttggtta acgatgatat atcctctcta tatatatttt atcaagtgat 540
tttaatgatt ggcacagtga ttggtcccgg aacgatattt ctcatgtt 588

<210> SEQ ID NO 6
<211> LENGTH: 185
<212> TYPE: DNA
<213> ORGANISM: Anthonomus grandis

<400> SEQUENCE: 6
aagtagacgc tcacgtatcc agaaggaaaa ccgtggcgga cttggcgaaa aacaaagaca 60
gaaaacgtgc agtcatcaac gacttggatt ccgcctttta aagcccgtat ggcaaaaaat 120
acgtaaagga gaagacgcgt ggagtggctt tacctaggaa aactttggca gcaattcaca 180
gaaga 185

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Asp Pro Asp Tyr Tyr Glu Phe Glu
1 5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Leu His Pro Gln Glu
1 5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Asp Gly Asp Ile Asp Phe
1 5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Gln Tyr Asp Gln Gly Glu Asp Arg Trp
1 5

<210> SEQ ID NO 11
<211> LENGTH: 8
<212> TYPE: PRT
<213> ORGANISM: Artificial Sequence
<220> FEATURE:

<223> OTHER INFORMATION: Synthetic peptide

<400> SEQUENCE: 11

Gly Pro Gly Thr Ile Phe Leu Met
1               5

<210> SEQ ID NO 12
<211> LENGTH: 63
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (63)..(63)
<223> OTHER INFORMATION: n is a, c, g, or t

<400> SEQUENCE: 12
gaattcacgc gtcgactagt agcatatgta cttttttttt tttttttttt tttttttttt     60 tvn                                                                   63

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t

<400> SEQUENCE: 13
gayccngayt aytaygartt ygar                                            24

<210> SEQ ID NO 14
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 14
ytcytgnggr tgna                                                       14

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t

<400> SEQUENCE: 15
gayggngaya tygaytty                                                   18

<210> SEQ ID NO 16

-continued

<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 16
catvaggaad atvgtdccgg gdccmar 27

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
ttaatcgttg tggatattta atag 24

<210> SEQ ID NO 18
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 18
gaaaaacatc cgggactaca cagtacgca 29

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
cggggatatt gatttccaac c 21

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tgacttacac caacttatcc 20

<210> SEQ ID NO 21
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 21
ccanckrtcy tcnccytgrt crtaytg 27

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
caaatttctc aaaaatcgcc acc 23

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
aacatgagaa atatcgttcc 20

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gggattttga aatcatactt ggta 24

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
gcgagcatca aaaaccatat cc 22

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 26
tccgaattca cgcgtcgact agtagca 27

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27
taatacgact cactataggg aga 23

<210> SEQ ID NO 28
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 28
taatacgact cactataggg agaatcacag gagcagcgtt gc 42

<210> SEQ ID NO 29
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 29
taatacgact cactataggg agaacaccaa cttatccaat atc 43

<210> SEQ ID NO 30
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 30
taatacgact cactataggg agatcaaatt tctcaaaatc g 41

<210> SEQ ID NO 31
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 31
taatacgact cactataggg agagcgagca tcaaaaacca tatc 44

<210> SEQ ID NO 32
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 32
taatacgact cactataggg agacggagac atcgatttcc aac 43

<210> SEQ ID NO 33
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 33
taatacgact cactataggg agaaacatga gaaatatcgt tcc 43

<210> SEQ ID NO 34
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 34
taatacgact cactataggg agaaagtaga cgctcacgta tcc 43

<210> SEQ ID NO 35
<211> LENGTH: 42

<212> TYPE: DNA
<213> ORGANISM: Artificial Sequence
<220> FEATURE:
<223> OTHER INFORMATION: Synthetic oligonucleotide

<400> SEQUENCE: 35
taatacgact cactataggg agatcttctg tgaattgctg cc 42

<210> SEQ ID NO 36
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 36
taatacgact cactataggg agagaactga actggcagac tatc 44

<210> SEQ ID NO 37
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 37
taatacgact cactataggg agagcgggta gatatcacac tctgt 45

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tgctcctgat agatttgatg 20

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
atccgggact acacagtacg ca 22

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
aaggcattaa cggtgacgac 20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41

-continued

```
tccaagtcgt tgatgactgc                                                 20


<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42

agatcgtcga gggtctgatg                                                 20


<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43

aaggcgggaa tgactttacc                                                 20


<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44

cctttaacac ccctgctatg                                                 20


<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45

tgaggtagtc ggtcaagtca                                                 20
```